United States Patent [19]

Ueda et al.

[11] Patent Number: 5,663,197
[45] Date of Patent: Sep. 2, 1997

[54] 2-(1-HYDROXYETHYL)-5-HYDROXYNAPHTHO[2,3-B]FURAN-4,9-DIONE AND ANTITUMOR AGENTS COMPRISING THIS COMPOUND

[75] Inventors: Shinichi Ueda; Harukuni Tokuda, both of Kyoto; Keiichi Hirai, Kanazawa; Heihachi Hatanaka, Nishinomiya, all of Japan

[73] Assignee: Taheebo Japan Co., Ltd., Osaka, Japan

[21] Appl. No.: 397,182

[22] PCT Filed: Sep. 10, 1993

[86] PCT No.: PCT/JP93/01292

§ 371 Date: Mar. 9, 1995

§ 102(e) Date: Mar. 9, 1995

[87] PCT Pub. No.: WO94/06786

PCT Pub. Date: Mar. 31, 1994

[30] Foreign Application Priority Data

Sep. 18, 1992 [JP] Japan ..................... 4-249340
Feb. 24, 1993 [JP] Japan ..................... 5-35251

[51] Int. Cl.$^6$ .................................................. A61R 31/34
[52] U.S. Cl. ............................................................ 514/468
[58] Field of Search ............................................... 514/468

[56] References Cited

PUBLICATIONS

Ueda et al., Phyto Chemistry, vol. 36, No. 2, pp. 323–325 (1994).
Chemical Abstracts III:160194e (1989).
Wagner et al, Helvetica Chimica Acta, vol. 72, pp. 659–667 (1989).
Fujimoto et al., J. Chem. Soc. Perkin Trans. 1, pp. 22323–22327 (1991).

*Primary Examiner*—Jerome D. Goldberg
*Attorney, Agent, or Firm*—Jacobson, Price, Holman & Stern, PLLC

[57] ABSTRACT

A novel antitumor compound, 2-(1-hydroxyethyl)-5-hydroxynaphto [2,3-b]furan-4,9-dione, having the following formula is provided.

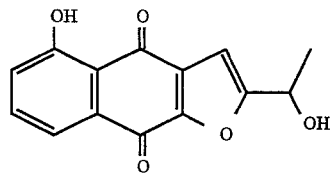

12 Claims, 29 Drawing Sheets

2-(1-HYDROXYETHYL)-5-HYDROXYNAPHTHO[2,3-B]FURAN-4,9-DIONE AND ANTITUMOR AGENTS COMPRISING THIS COMPOUND

The present invention relates to a novel compound possessing antitumor activity, and an antitumor agent comprising said compound.

The mortality from cancers continues to increase every year, and cancers are major causes of deaths in advanced countries. Control of cancers is therefore the greatest interest in the medical field. Development of antitumor agents has been one of the important themes for cancer therapy, and a variety of anticancer agents have been developed so far. Thus, many antitumor antibiotics and other antitumor agents, which directly act on tumor cells and produce a cytocidal effect on the cells, have been developed. However, these agents are also highly cytotoxic to normal cells or tissues, and severe side effects have been unavoidable in the majority of cases. Accordingly, the development of an antitumor agent which has selective cytotoxicity against tumor cells but shows few side effects has long been researcher's ambition.

Although tumor cells have not been fully characterized, it is considered that dormant oncogenes on chromosomes are expressed as a result of stimulation by carcinogenic chemicals, radiation, ultraviolet rays or carcinogenic viruses, or conversely, as a result of inactivation of tumor suppressor genes by such stimulation. It is believed that intra- and extra-cellular secretion of expression products of the oncogenes or their attachment to cell membranes is related to the acquisition of the neoplastic properties specific to tumor cells, such as metastasis, infiltration ability and uncontrolled proliferation. If any method to inhibit one of the processes caused by the abnormal expression becomes available, such a method is expected to provide an effective tool for controlling cancers.

In Japan, candidates for antitumor agents have been screened for their effectiveness according to the NCI (U.S. National Cancer Institute) antitumor drug screening protocol using mouse leukemia cell lines L1210 and P388. However, the results of the screening test have frequently been inconsistent with the corresponding therapeutic results in patients suffering from cancers. Recently modified new NCI screening protocol uses human cancer cell lines, and good correlation has been found between the results of the new test and therapeutic results in clinical studies [G. B. Grindey: Cancer Cells 2 (6): p.163–171, 1990; N. Saijo, Clinician 17 (6): p.4–9, 1991].

As the results of screening of a variety of compounds for their antitumor activities by means of the new NCI screening protocol using human cancer cell lines, the present inventors have found that 2-(1-hydroxyethyl)-5-hydroxynaphtho[2,3-b]furan-4,9-dione (referred to as NFD hereinafter), a novel compound extracted from *Tabebuia avellanedae Lorentz, ex Griseb.*, which belongs to the family Bignoniaceae, has excellent antitumor activity. The present invention has been completed based on the findings.

Accordingly, an object of the present invention is to provide NFD, a novel compound having the following formula (1).

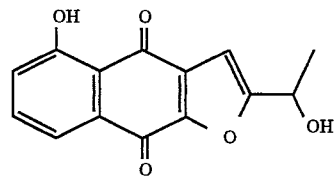

It is a further object of this invention to provide antitumor agents comprising NFD as an active ingredient.

It is yet another object of the present invention to provide the process for manufacturing NFD comprising the steps of: extracting the dried bark of *Tabebuia avellanedae Lorentz, ex Griseb.* with hot methanol; extracting a residue obtained by evaporation of the extract with cold chloroform; and separating chloroform-soluble components by preparative thin-layer chromatography using toluene/ethyl acetate (4:1) as a developing solvent system.

NFD (molecular formula: $C_{14}H_{10}O_5$; molecular weight: 258.230) occurs as yellow needles with a melting point of 181° C., which is freely soluble in dimethylsulfoxide and chloroform and slightly soluble in water.

NFD remarkably inhibits the growth of the following tumor cells at low concentrations and exhibits selective toxicity to these tumor cells: cultured human lung adenocarcinoma cell lines A-549, VMRC-LCD and SK-LU-1, human lung squamous cell carcinoma Calu-1 cells, human colon adenocarcinoma WiDr cells, human prostate cancer LNCaP cells, human vaginal squamous cell carcinoma A-431 cells, human cervical carcinoma HeLa cells, human cholangiocarcinoma HuCC-T1 cells, mouse skin cancer melanoma B16 (M4) cells, human malignant B-cell lymphoma cells, human chronic myelogenous leukemia K562 cells, human pancreatic carcinoma ASPC-1 cells, human neuroblastoma IMR-132 cells, human lung small cell carcinoma SCCH-194 cells, human urinary bladder carcinoma T24 cells, human renal cell carcinoma VMRC-RCW cells, human gastric cancer NUGC-2 cells, human thyroid carcinoma 8305C cells, human breast cancer MRK-nu-1 cells, human hepatoma HUH-7 cells, human ovarian carcinoma TYK-nu cells and human chorio carcinoma BeWo cells.

The $LD_{50}$ values (50% growth inhibitory dose: synonymous with $IC_{50}$) of NFD for the above malignant tumor cells were within the range of about 5.5–25 ng/ml. Meanwhile, the $LD_{50}$ values ($IC_{50}$ values) for cultured normal human N6KA fibroblasts, normal human tracheal epithelial cells, normal human renal cells and normal human lymphocytes are within the range of 55–84 ng/ml. As for general toxicology, the $LD_{50}$ value of NFD for ICR mice (male) is 0.73 mg/100 g body weight when intraperitoneally administered, and 0.84 mg/100 g body weight when orally administered.

As described above, NFD is an excellent antitumor drug against various types of cancers with a minimal risk of side effects. NFD was also found to interfere with the promotion stage, the most important process of transition of normal cells to cancer cells, initiated with chemical carcinogens or viruses, and to function as an anti-carcinogenic promoter during the process of carcinogenesis. The term "antitumor agents" used in the present specification is intended to include drugs which are effective in producing cure or palliation in all types of malignant tumors, such as solid tumors, hematologic neoplasms and sarcomas, and in preventing the generation of these malignant tumors.

Figure 1:
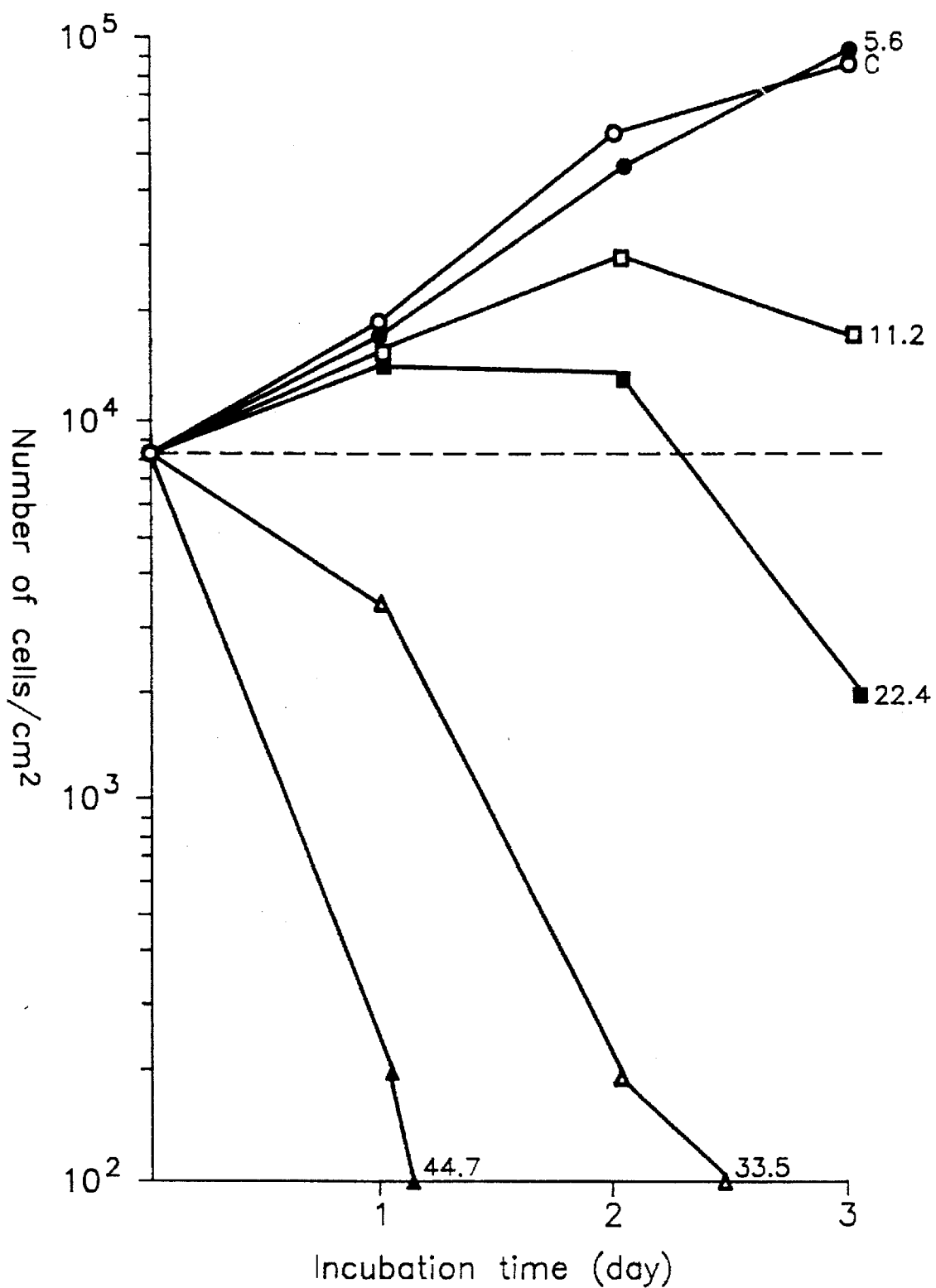
FIG. 1 shows the growth inhibitory and lethal effects of NFD on human lung adenocarcinoma A-549 cells.
Figure 2:
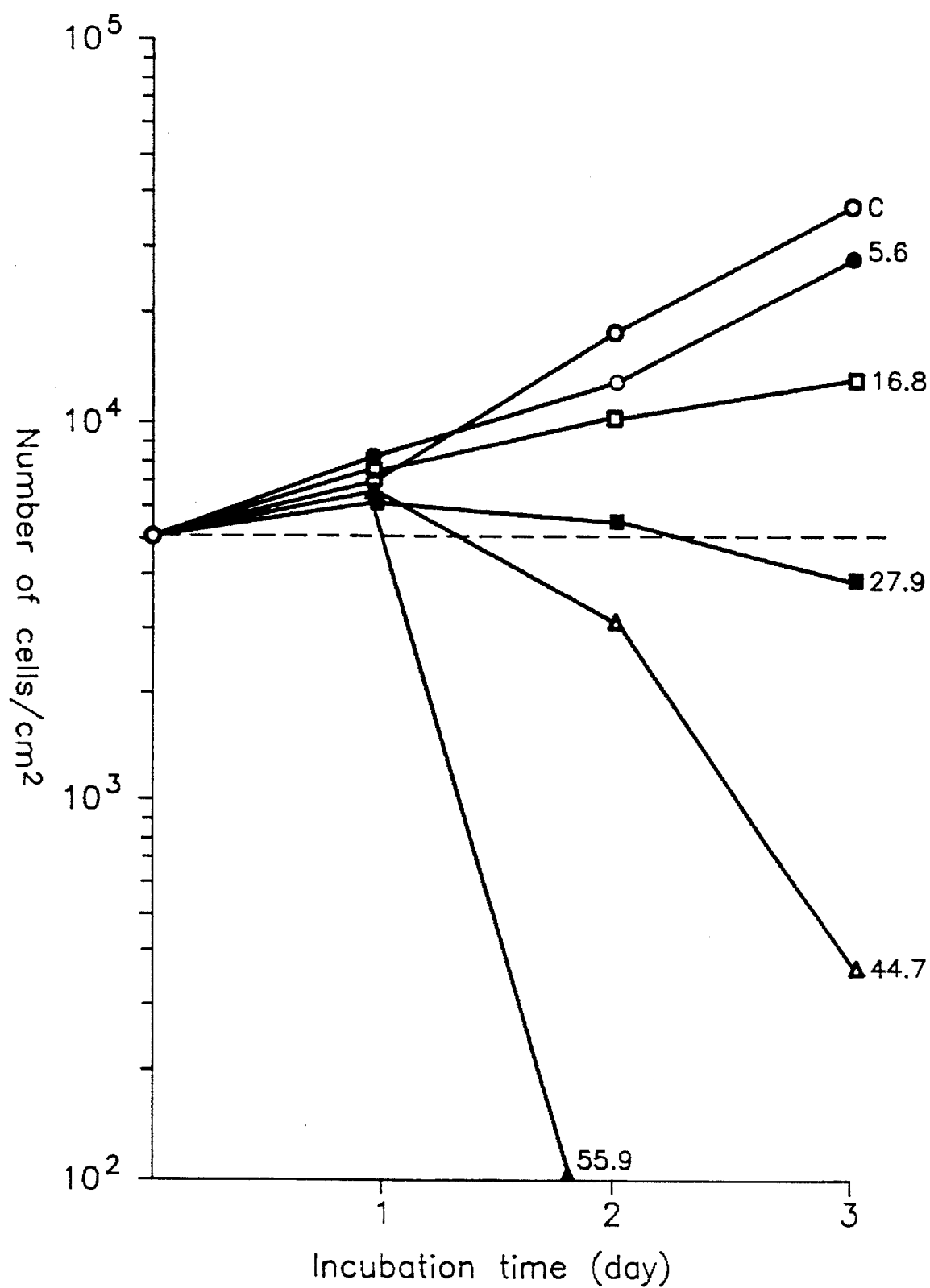
FIG. 2 shows the growth inhibitory and lethal effects of NFD on human lung adenocarcinoma VMRC-LCD cells.

Following working Examples illustrate the present invention in more detail.

EXAMPLE 1

Production of NFD

One kg of dried bark of *Tabebuia avellanedae Lorentz, ex. Griseb.* (producing country: Brazil; commercially available from Taheebo Japan Co., Ltd., Japan) was cut to pieces, and extracted with three 1000-ml portions of methanol under reflux for 30 minutes, and the solvent was evaporated off under reduced pressure. The residue (145 g) was soaked in three 400-ml portions of cold chloroform, and the chloroform layer was washed with water and dried over anhydrous magnesium sulfate, to yield 1 g of a residue after evaporation of the solvent. The residue was subjected to preparative thin-layer chromatography on TLC plate coated with silica gel 60$F_{254}$, 0.5 mm thick, using a mixture of toluene: ethyl acetate (4:1 v/v) as a developing solvent. The spot at Rf=0.24 was scraped off and extracted with a mixture of chloroform-methanol (9:1 v/v) to yield NFD. This TLC procedure was repeated, and a total of 0.8 mg of NFD was obtained. Melting point: 181° C.

EXAMPLE 2

Antitumor Activity of NFD on Various Types of Malignant Tumor Cells Including Human Solid Tumor Cells, Hematologic Neoplasms and Sarcomas

(1) Preparation of Test Samples

An appropriate amount of NFD was dissolved in DMSO to give a 1.0 mg/ml stock solution, which was diluted as necessary before use.

(2) In Vitro Antitumor Test of NFD (Growth Inhibitory Action and Lethal Activity)

The antitumor effect of NFD on human cancer cells and mouse cancer cells was assessed according to the following methods.

The following cells in the late logarithmic phase were harvested after treatment with trypsin (containing 0.25% trypsin and 0.02% EDTA; 37° C., 3 min) and used in the test: human lung adenocarcinoma cell lines A-549, VMRC-LCD and SK-LU-1, human lung squamous cell carcinoma Calu-1 cells, human colon adenocarcinoma WiDr cells, human prostate cancer LNCaP cells, human vaginal squamous cell carcinoma A-431 cells, human cervical carcinoma HeLa cells, human cholangiocarcinoma HuCC-T1 cells, mouse skin cancer melanoma B16 (M4) cells, human pancreatic carcinoma ASPC-1 cells, human neuroblastoma IMR-132 cells, human lung small cell carcinoma SCCH-194 cells, human urinary bladder carcinoma T24 cells, human renal cell carcinoma VFLRC-RCW cells, human gastric cancer NUGC-2 cells, human thyroid carcinoma 8305C cells, human hepatoma HUH-7 cells, human ovarian carcinoma TYK-nu cells and human chorio carcinoma BeWo cells. Suspension cultures of human breast cancer MRK-nu-1 cells, human malignant B-cell lymphoma cells and human chronic myelogenous leukemia K562 cells were used to harvest the cells to be used in the test. Meanwhile, normal human N6KA fibroblasts were harvested after trypsinization at the late logarithmic phase, normal human tracheal epithelial cells and renal cells were collected directly from the tracheal and renal tissues, and normal human lymphocytes were collected from peripheral blood of normal adult donors. These cells were plated onto a 96-well microplate at a density of 5–10×$10^3$ cells/$cm^2$ using DMEM or RPMI-1640 medium containing 10% fetal bovine serum and cultured for 24 hours in a conventional manner, after which a pre-determined amount of NFD dissolved in DMSO was added to each well. Cultivation was continued, and the number of viable cells was counted after 24, 48 and 72 hours. To eliminate a possible adverse effect of DMSO used as the solvent for NFD, the final concentration of DMSO in the culture medium was adjusted to 0.5% or below, at which no toxicity occurs. The wells to which DMSO alone was added served as the control.

(3) Enumeration of Viable Cells

Tumor cells grown on the 96-well microplate were harvested after trypsinization, and 0.25% trypan blue was added thereto. Cells that remained unstained were regarded as viable cells, and cells that were stained blue were regarded as dead cells (trypan blue exclusion test).

(4) Tumor Cells and Normal Cells Used in the Test a) Human lung adenocarcinoma (A-549 cells)

Human lung adenocarcinoma A-549 cells were obtained from Flow Labo Inc. The cells were subcultured, in DEEM medium containing 50 IU/ml penicillin and 50 µg/ml streptomycin and supplemented with 10% fetal bovine serum, at 37° C. under 5% $CO_2$ atmosphere and used in the test.

b) Human lung adenocarcinoma (VMRC-LCD cells)

Human lung adenocarcinoma VMRC-LCD cells were obtained from National Institute of Hygienic Sciences. The cells were subcultured, in DMEM medium containing 50 IU/ml penicillin and 50 µ/ml streptomycin and supplemented with 10% fetal bovine serum, at 37° C. under 5% $CO_2$ atmosphere and used in the test.

c) Human lung adenocarcinoma (SK-LU-1 cells)

Human lung adenocarcinoma SK-LU-1 cells were obtained from Radiation Hazard Research Institute. The cells were subcultured, in DMEM medium containing 50 IU/ml penicillin and 50 µ/ml streptomycin and supplemented with 10% fetal bovine serum, at 37° C. under 5% $CO_2$ atmosphere and used in the test.

d) Human lung squamous epithelioma (Calu-1 cells)

Human lung squamous epithelioma Calu-1 cells were obtained from Radiation Hazard Research Institute. The cells were subcultured, in DMEM medium containing 50 IU/ml of penicillin and 50 µ/ml streptomycin and supplemented with 10% fetal bovine serum, at 37° C. under 5% $CO_2$ atmosphere and used in the test.

e) Human colon adenocarcinoma (WiDr cells)

Human colon adenocarcinoma WiDr cells were obtained from Hatano Laboratory, Biosafety Research Center, Foods and Drugs. The cells were subcultured, in DMEM medium containing 50 IU/ml penicillin and 50 µ/ml streptomycin and supplemented with 10% fetal bovine serum, at 37° C. under 5% $CO_2$ atmosphere and used in the test.

f) Human prostate cancer (LNCaP cells)

Human prostate cancer LNCaP cells were obtained from the Department of Endocrinology, Kagawa Medical School. The cells were cultured in RPMI-1640 medium containing 10% fetal bovine serum at 37° C. under 5% $CO_2$ atmosphere and used in the test.

g) Human vaginal squamous cell carcinoma (A-431 cells)

Human vaginal squamous cell carcinoma A-431 cells were obtained from the Department of Biochemistry, Kanazawa Medical University. The cells were cultured in RPMI-1640 medium containing 10% fetal bovine serum at 37° C. under 5% $CO_2$ atmosphere and used in the test.

h) Human cervical carcinoma (HeLa cells)

Human cervical carcinoma HeLa cells were obtained from Flow Labo Inc. The cells were cultured in DMEM medium containing 10% fetal bovine serum at 37° C. under 5% $CO_2$ atmosphere and used in the test.

i) Human cholangiocarcinoma (HuCC-T1 cells)

Human cholangiocarcinoma HuCC-T1 cells were obtained from the Department of Biochemistry, Kanazawa Medical University. The cells were cultured in RPMI-1640 medium containing 10% fetal bovine serum at 37° C. under 5% $CO_2$ atmosphere and used in the test.

j) Mouse skin cancer (melanoma)

Mouse melanoma B16 (M4) cells were obtained from the Department of Biochemistry, Kanazawa Medical University. The cells were cultured in DMEM medium containing 10% fetal bovine serum at 37° C. under 5% $CO_2$ atmosphere and used in the test.

k) Human malignant lymphoma

Human malignant B-cell lymphoma cells were obtained from the Department of internal Medicine, Kanazawa Medical University. The cells were cultured in RPMI-1640 medium containing 10% fetal bovine serum at 37° C. under 5% $CO_2$ atmosphere and used in the test.

l) Human chronic myelogenous leukemia (K562 cells)

Human chronic myelogenous leukemia K562 cells were obtained from the Department of Internal Medicine, Kanazawa Medical University. The cells were cultured in RPMI-1640 medium containing 10% fetal bovine serum at 37° C. under 5% $CO_2$ atmosphere and used in the test.

m) Human pancreatic carcinoma (ASPC-1 cells)

Human pancreatic carcinoma ASPC-1 cells were obtained from Flow Labo. Inc. The cells were subcultured in RPMI-1640 medium containing 10% fetal bovine serum at 37° C. under 5% $CO_2$ atmosphere and used in the test.

n) Human neuroblastoma (IMR-132 cells)

Human neuroblastoma IMR-132 cells were obtained from National Institute of Hygienic Sciences. The cells were subcultured, in DMEM medium containing 1% NEAA, 50 IU/ml penicillin and 50 µ/ml streptomycin and supplemented with 10% fetal bovine serum, at 37° C. under 5% $CO_2$ atmosphere and used in the test.

o) Human lung small cell carcinoma (SCCH-194 cells)

Human lung small cell carcinoma SCCH-194 cells were obtained from Radiation Hazard Research Institute. The cells were subcultured, in ES medium containing 60 µ/ml of kanamycin sulfate and supplemented with 10% fetal bovine serum, at 37° C. under 5% $CO_2$ atmosphere and used in the test.

p) Human uninary bladder carcinoma (T24 cells)

Human uninary bladder carcinoma T24 cells were obtained from Kihara Biological Research Institute, Yokohama City University. The cells were subcultured in MEM medium containing 10% fetal bovine serum at 37° C. under 5% $CO_2$ atmosphere and used in the test.

q) Human renal cell carcinoma (VMRC-RCW cells)

Human renal cell carcinoma VMRC-RCW cells were obtained from Radiation Hazard Research Institute. The cells were cultured, in MEM medium containing 1% NEAA and 4 mM HEPES and supplemented with 10% fetal bovine serum, at 37° C. under 5% $CO_2$ atmosphere and used in the test.

r) Human gastric cancer (NUGC-2 cells)

Human gastric cancer NUGC-2 cells were obtained from Radiation Hazard Research institute. The cells were cultured, in RPMI-1640 medium containing 4 mM HEPES and supplemented with 10% fetal bovine serum, at 37° C. under 5% $CO_2$ atmosphere and used in the test.

s) Human thyroid carcinoma (8305C cells)

Human thyroid carcinoma 8305C cells were obtained from Radiation Hazard Research Institute. The cells were cultured, in MEM medium containing 1% NEAA and 4 mM HEPES and supplemented with 10% fetal bovine serum, at 37° C. under 5% $CO_2$ atmosphere and used in the test.

t) Human breast cancer (MRK-nu-1 cells)

Human breast cancer MRK-nu-1 cells were obtained from University of Tokyo Medical Science Research Institute. The cells were cultured in DM-160 medium containing 10% fetal bovine serum at 37° C. under 5% $CO_2$ atmosphere and used in the test.

u) Human hepatoma (HUH-7 cells)

Human hepatoma HUH-7 cells were obtained from Cancer Research Institute, Okayama University. The cells were cultured, in RPMI-1640 medium containing 0.2% lactalbumin hydrolysate and supplemented with 1% fetal bovine serum, at 37° C. under 5% $CO_2$ atmosphere and used in the test.

v) Human ovarian carcinoma (TYK-nu cells)

Human ovarian carcinoma TYK-nu cells were obtained from Hatano Laboratory, Biosafety Research Center, Foods and Drugs. The cells were cultured in MEM medium containing 10% fetal bovine serum at 37° C. under 5% $CO_2$ atmosphere and used in the test.

w) Human chorio carcinoma (BeWo cells)

Human chorio carcinoma BeWo cells were obtained from National Institute of Hygienic Sciences. The cells were cultured in Ham's F12 (K) medium containing 15% fetal bovine serum at 37° C. under 5% $CO_2$ atmosphere and used in the test.

x) Normal human fibroblasts (N6KA cells)

Normal human N6KA fibroblasts were obtained from Department of Biochemistry, Kanazawa Medical University. The cells were cultured, in DMEM medium containing 50 IU/ml penicillin and 50 µ/ml streptomycin and supplemented with 10% fetal bovine serum, at 37° C. under 5% $CO_2$ atmosphere and used in the test.

y) Normal human tracheal epithelial cells

Normal human tracheal epithelial cells were collected after trypsinization of tracheal epithelium obtained from autopsy samples in Kanazawa Medical University Hospital. The cells were cultured, in DMEM medium containing 50 IU/ml penicillin and 50 µ/ml streptomycin and supplemented with 10% fetal bovine serum, at 37° C. under 5% $CO_2$ atmosphere and used in the test.

z) Normal human peripheral blood lymphocytes

Normal human peripheral blood lymphocytes were isolated by Ficoll-Hypaque gradient centrifugation of peripheral blood samples obtained from normal adult donors. Lymphocytes were plated onto a 96-well microplate at a density of $5 \times 10^3$ cells/cm²/well using RPMi-1640 medium containing 10% fetal bovine serum, cultured at 37° C. under 5% $CO_2$ atmosphere and used in the test.

aa) Normal human renal cells

Normal human renal cells were isolated after collagenase treatment of a kidney nephrectomized due to tumors or other reasons at the Department of Urology, Kanazawa Medical University. The cells were cultured, in MEM medium containing 1% NEAA, 4 nM HEPES and 60 µg/ml kanamycin sulfate and supplemented with 10% fetal bovine serum, at 37° C. under 5% $CO_2$ atmosphere and used in the test.

(5) Test Results

Growth inhibitory action and lethal activity of NFD on various types of malignant tumor cells and normal human cells listed above were evaluated by counting the number of viable cells in each well of the 96-well microplate. Growth of cells cultured in the medium containing no NFD was used as a control. The results are shown in FIGS. 1–27. The meanings of symbols used in the figures are given below.

In FIG. 1, the concentrations of NFD in the medium are as follows: o—o: NFD-free control (C); ●—●: 5.6 ng/ml; □—□: 11.2 ng/ml; ml: ■—■: 22.4 ng/ml; ∆—∆: 33.5 ng/ml; ▲—▲: 44.7 ng/ml In FIG. 2, the concentrations of NFD in the medium are as follows: o—o: NFD-free control (C); ●—●: 5.6 ng/ml; □—□: 16.8 ng/ml; ■—■: 27.9 ng/ml; ∆—∆: 44.7 ng/ml; ▲—▲: 55.9 ng/ml.

Figure 3:
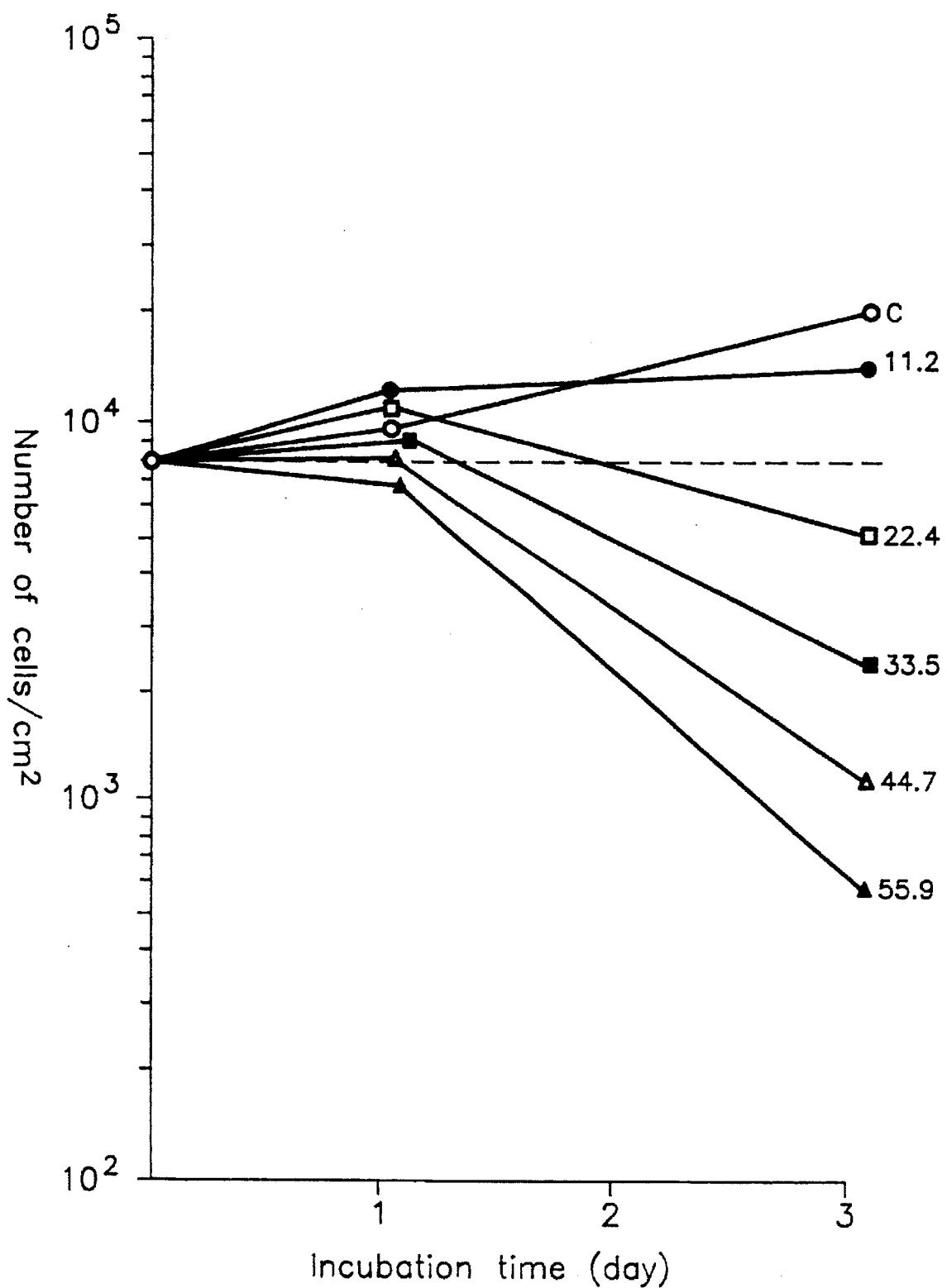
FIG. 3 shows the growth inhibitory and lethal effects of NFD on human lung adenocarcinoma SK-LU-1 cells.

In FIG. 3, the concentrations of NFD in the medium are as follows: o—o: NFD-free control (C); ●—●: 11.2 ng/ml; □—□: 22.4 ng/ml; ■—■: 33.5 ng/ml; ∆—∆: 44.7 ng/ml; ▲—▲: 55.9 ng/ml.

Figure 4:
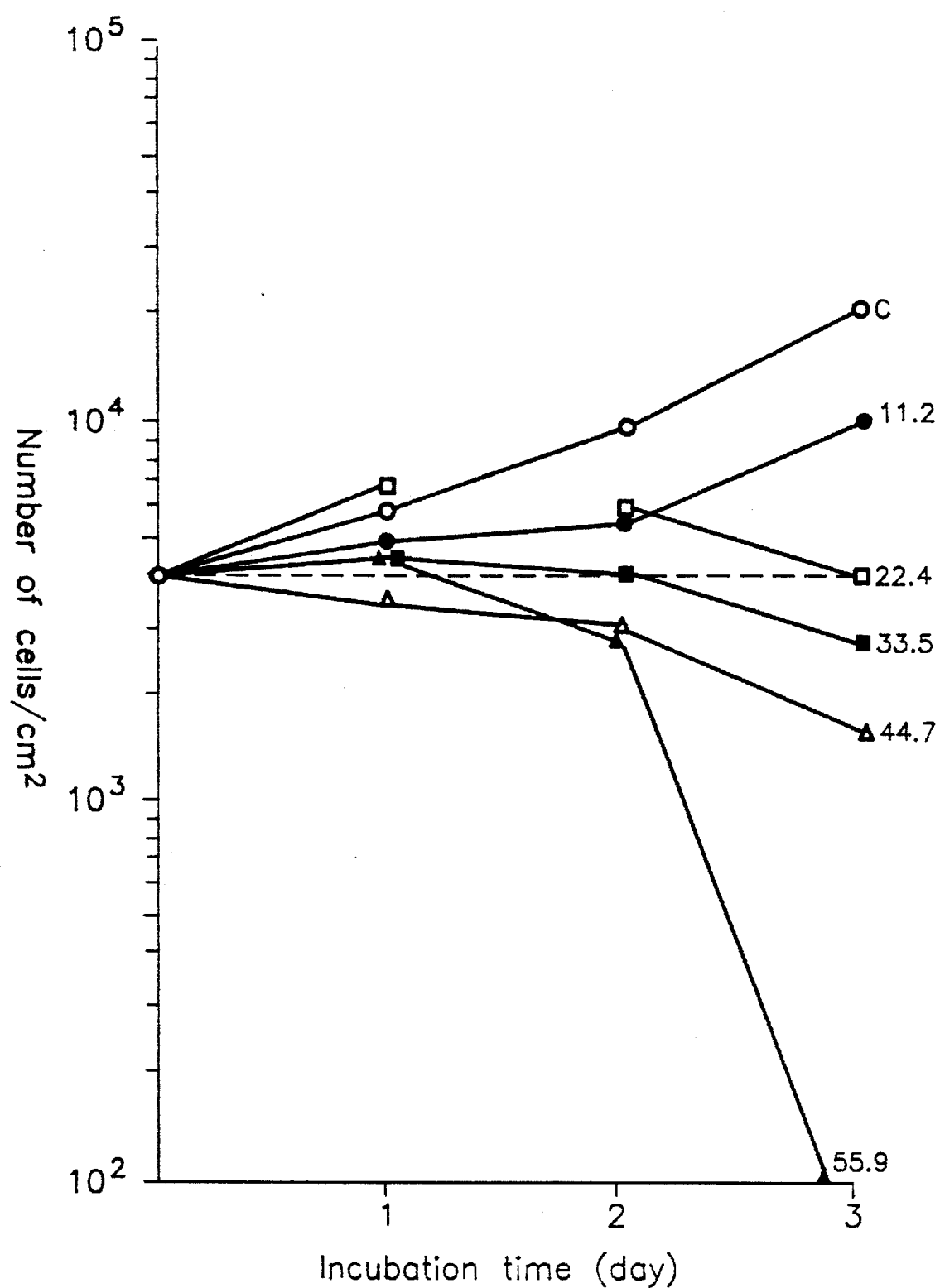
FIG. 4 shows the growth inhibitory and lethal effects of NFD on human lung squamous cell carcinoma Calu-1 cells.

In FIG. 4, the concentrations of NFD in the medium are as follows: o—o: NFD-free control (C); ●—●: 11.2 ng/ml; □—□: 22.4 ng/ml; ■—■: 33.5 ng/ml; ∆—∆: 44.7 ng/ml; ▲—▲: 55.9 ng/ml.

As shown in FIGS. 1–4, NFD was found to inhibit the growth of human lung cancer cells almost completely at 11.2–16.8 ng/ml and to cause necrosis in almost all tumor cells at 33.5–55.4 ng/ml.

Figure 5:
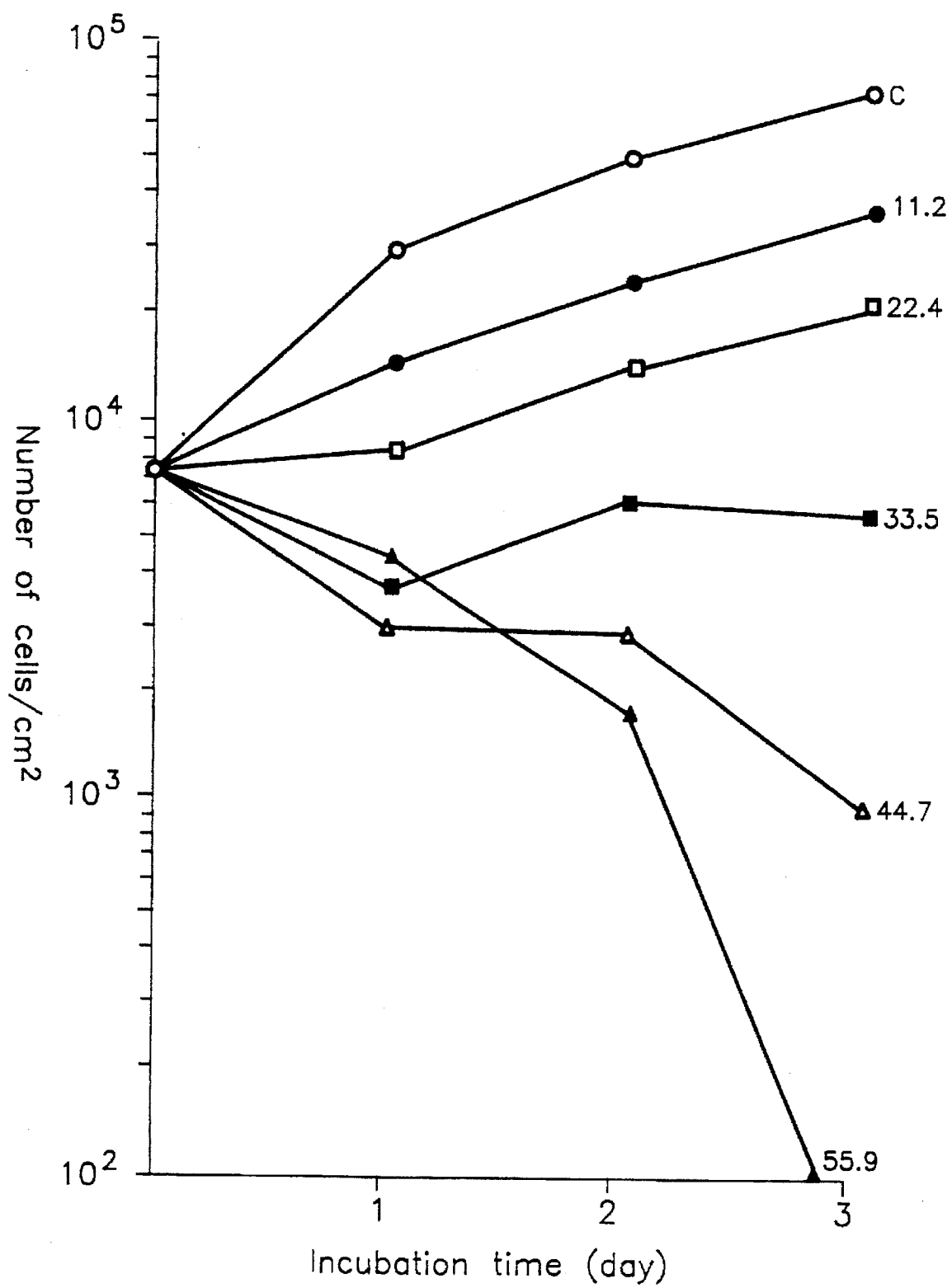
FIG. 5 shows the growth inhibitory and lethal effects of NFD on human colon adenocarcinoma WiDr cells.

In FIG. 5, the concentrations of NFD in the medium are as follows: o—o: NFD-free control (C); ●—●: 11.2 ng/ml; □—□: 22.4 ng/ml: ■—■: 33.5 ng/ml; ∆—∆: 44.7 ng/ml; ▲—▲: 55.9 ng/ml.

As shown in FIG. 5, NFD was found to inhibit the growth of human colon adenocarcinoma cells almost completely at 22.4–33.5 ng/ml and to cause necrosis in almost all tumor cells at 44.7–55.9 ng/ml.

Figure 6:
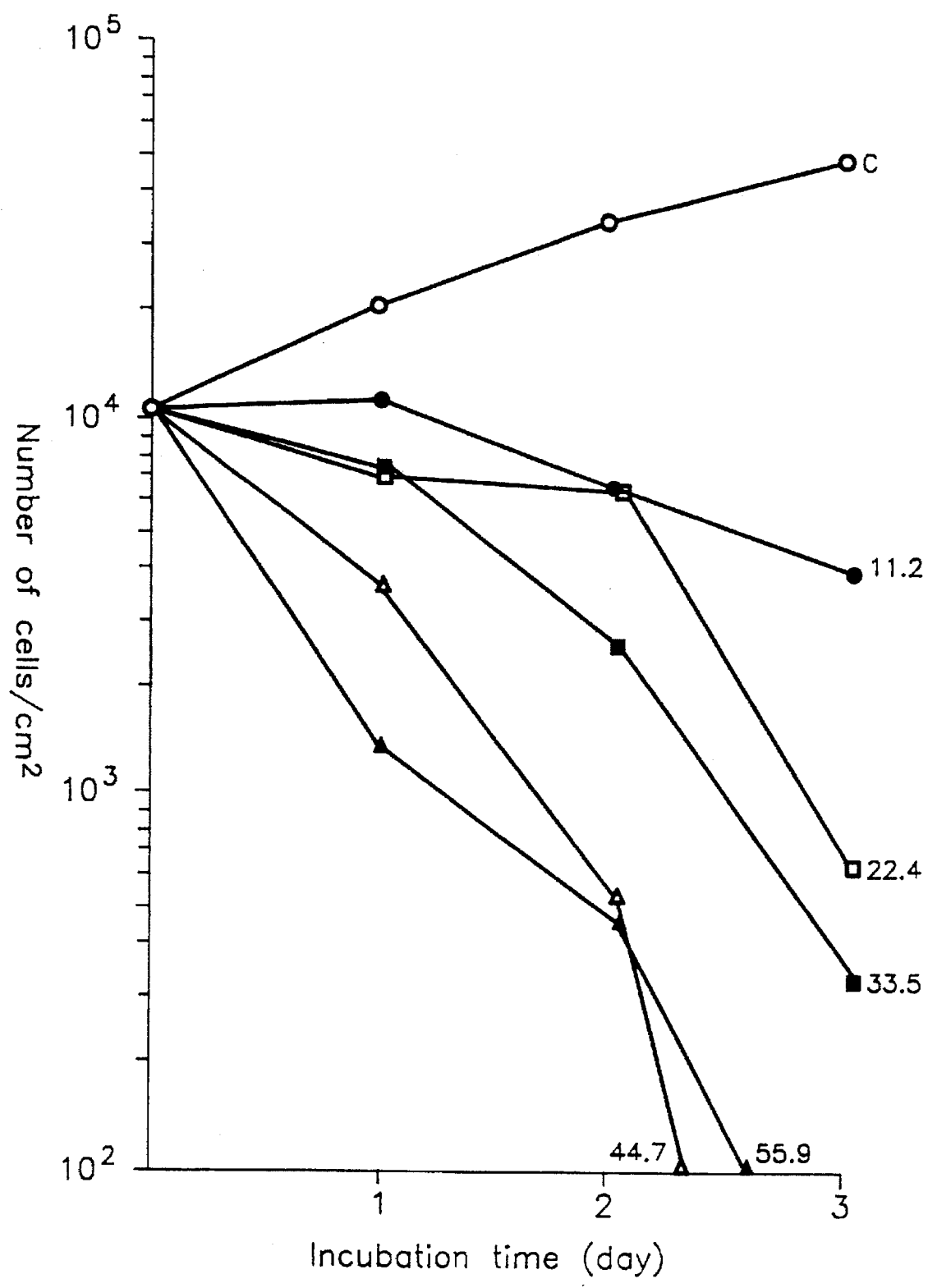
FIG. 6 shows the growth inhibitory and lethal effects of NFD on human prostate cancer LNCaP cells.

In FIG. 6, the concentrations of NFD in the medium are as follows: o—o: NFD-free control (C); ●—●: 11.2 ng/ml; □—□: 22.4 ng/ml; ■—■: 33.5 ng/ml; ∆—∆: 44.7 ng/ml; ▲—▲: 55.9 ng/ml.

As shown in FIG. 6, NFD was found to inhibit the growth of human colon adenocarcinoma cells almost completely at 11.2 ng/ml and to cause necrosis in almost all tumor cells at 22.4–55.9 ng/ml.

Figure 7:
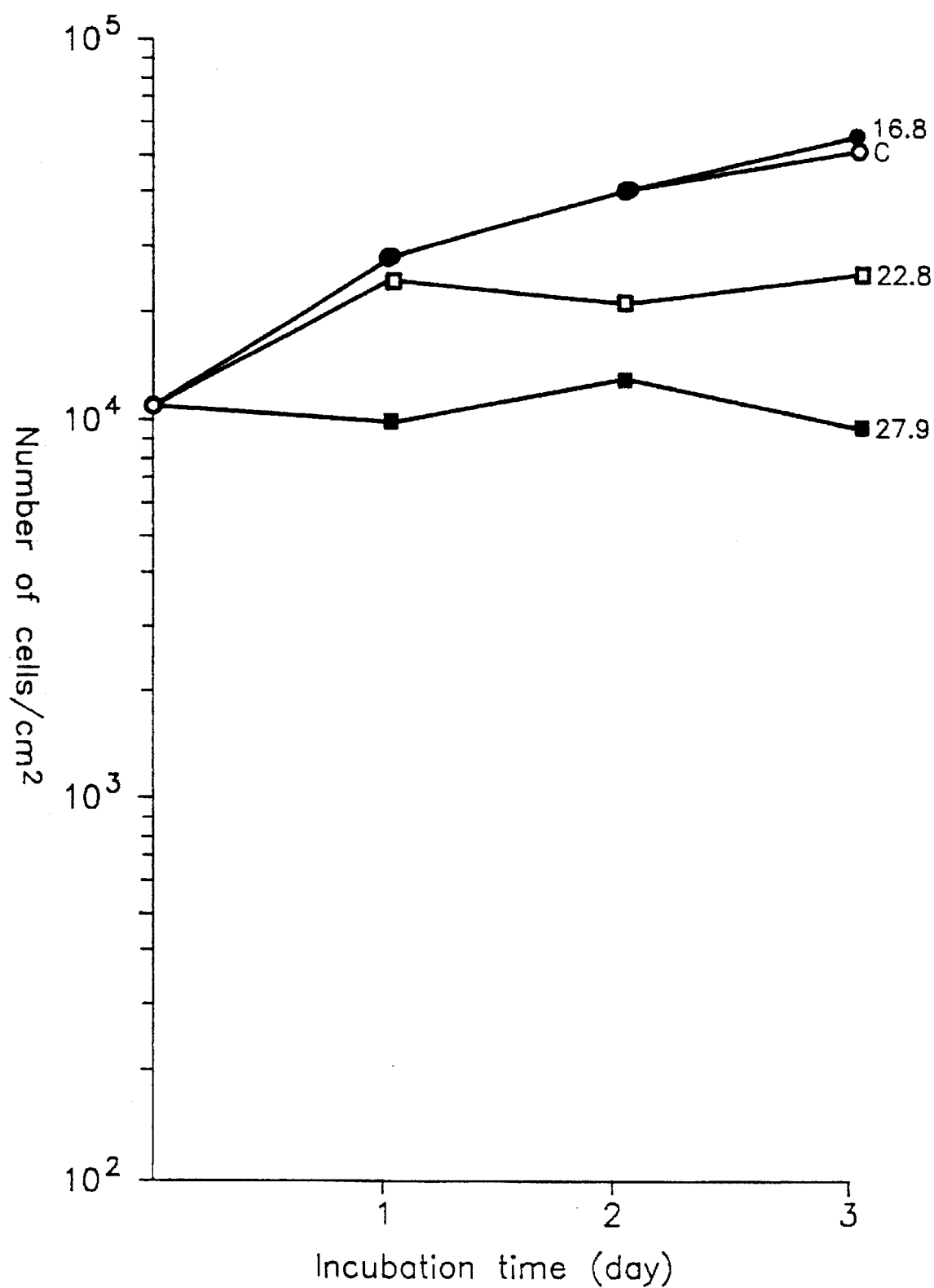
FIG. 7 shows the growth inhibitory and lethal effects on human vaginal squamous cell carcinoma A-431 cells.

In FIG. 7, the concentrations of NFD in the medium are as follows: o—o: NFD-free control (C); ■—■: 16.8 ng/ml; □—□: 22.8 ng/ml; ■—■: 27.9 ng/ml.

As shown in FIG. 7, NFD was found to inhibit the growth of human vaginal squamous cell carcinoma cells almost completely at 27.9 ng/ml.

Figure 8:
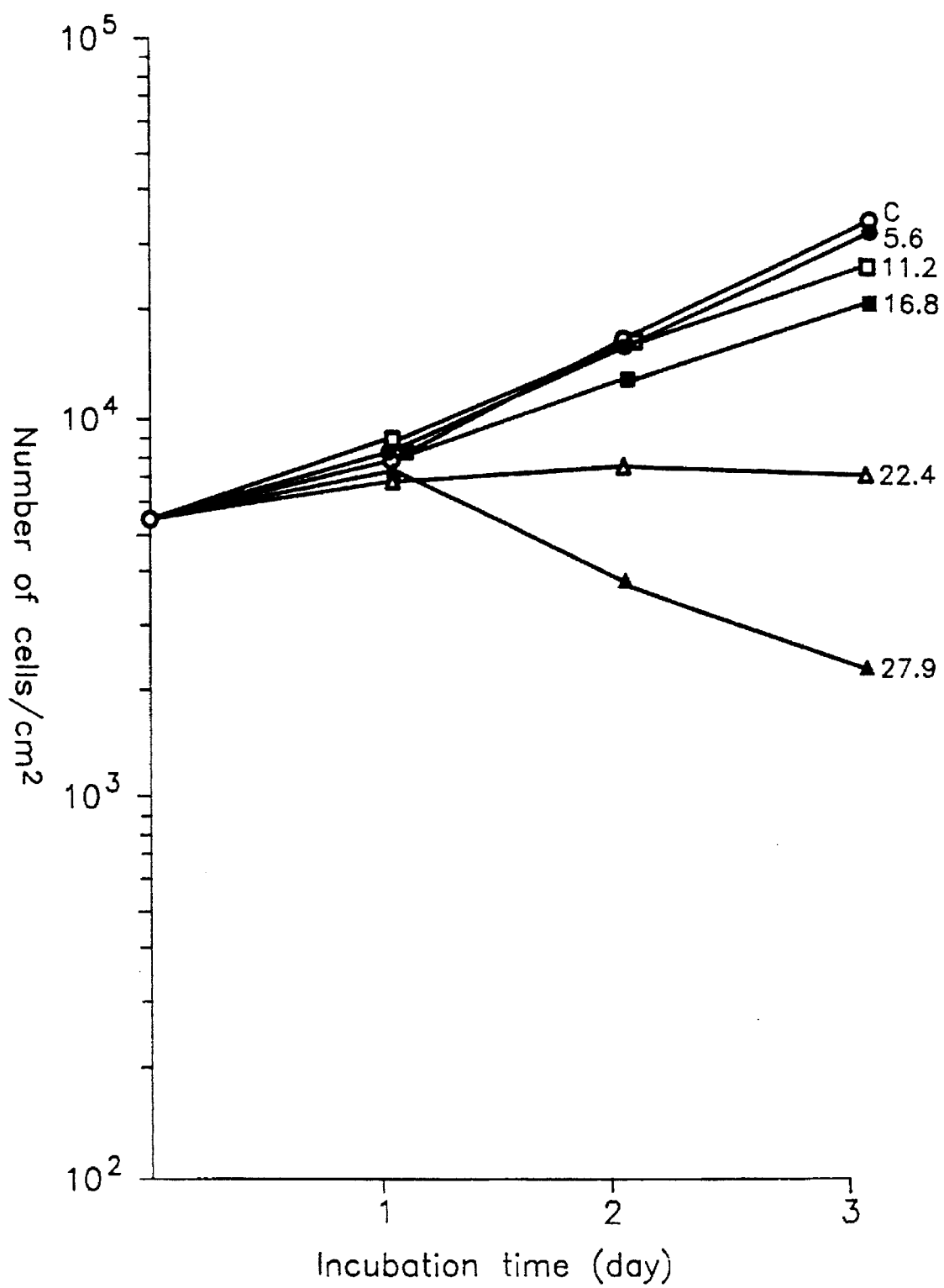
FIG. 8 shows the growth inhibitory and lethal effects of NFD on human cervical carcinoma HeLa cells.

In FIG. 8, the concentrations of NFD in the medium are as follows: o—o: NFD-free control (C); ●—●: 5.6 ng/ml; □—□: 11.2 ng/ml; ■—■: 16.8 ng/ml; ∆—∆: 22.4 ng/ml; ▲—▲: 27.9 ng/ml.

As shown in FIG. 8, NFD was found to inhibit the growth of human cervical carcinoma cells almost completely at 22.4 ng/ml and to cause necrosis in these tumor cells at 27.9 ng/ml.

Figure 9:
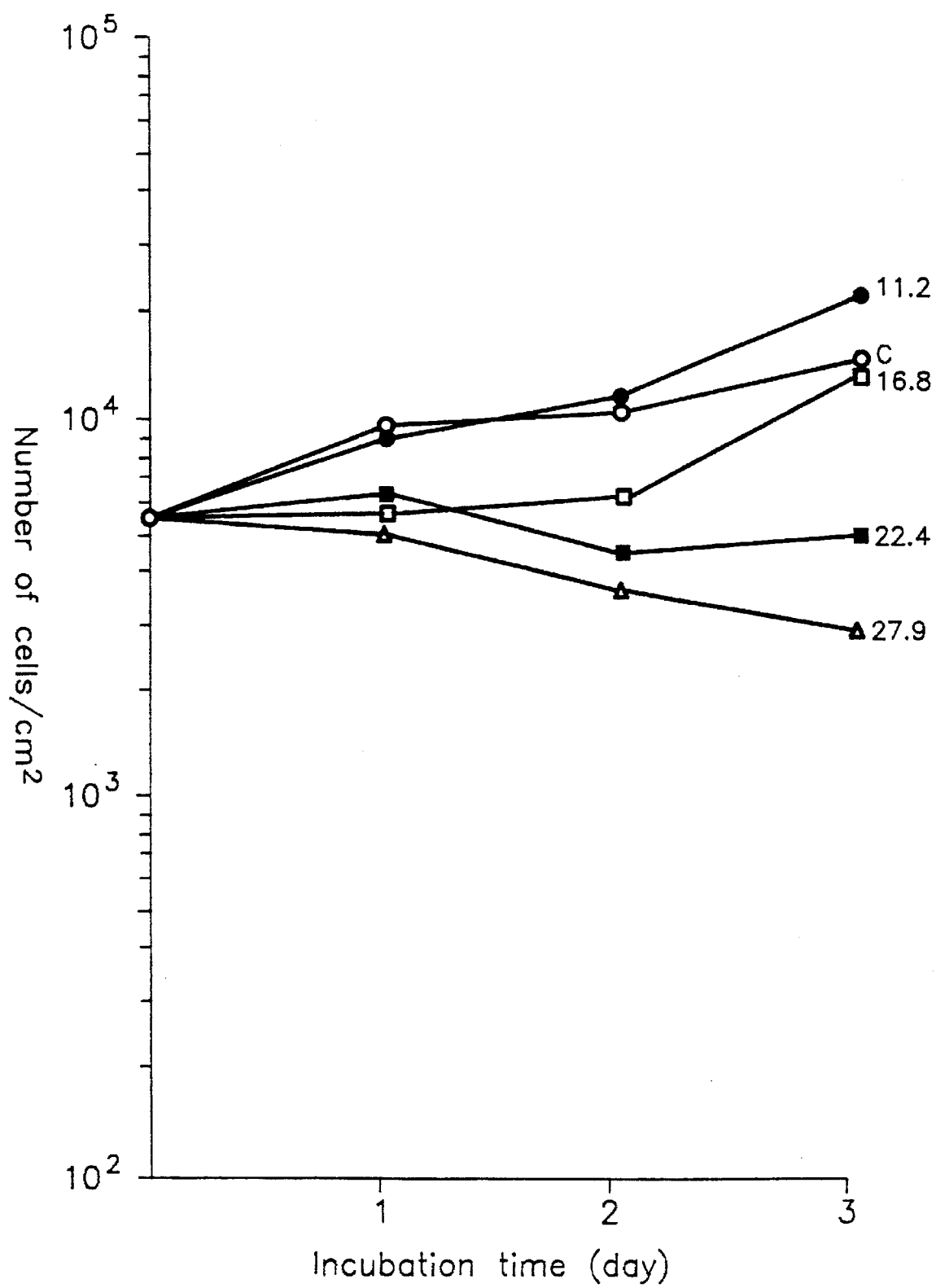
FIG. 9 shows the growth inhibitory and lethal effects of human cholangiocarcinoma HuCC-T1 cells.

In FIG. 9, the concentrations of NFD in the medium are: o—o: NFD-free control (C); ●—●: 11.2 ng/ml; □—□: 16.8 ng/ml; ■—■: 22.4 ng/ml; ∆—∆: 27.9 ng/ml.

As shown in FIG. 9, NFD was found to inhibit the growth of human cholangiocarcinoma cells almost completely at 22.4 ng/ml and to cause necrosis in these tumor cells at 27.9 ng/ml.

Figure 10:
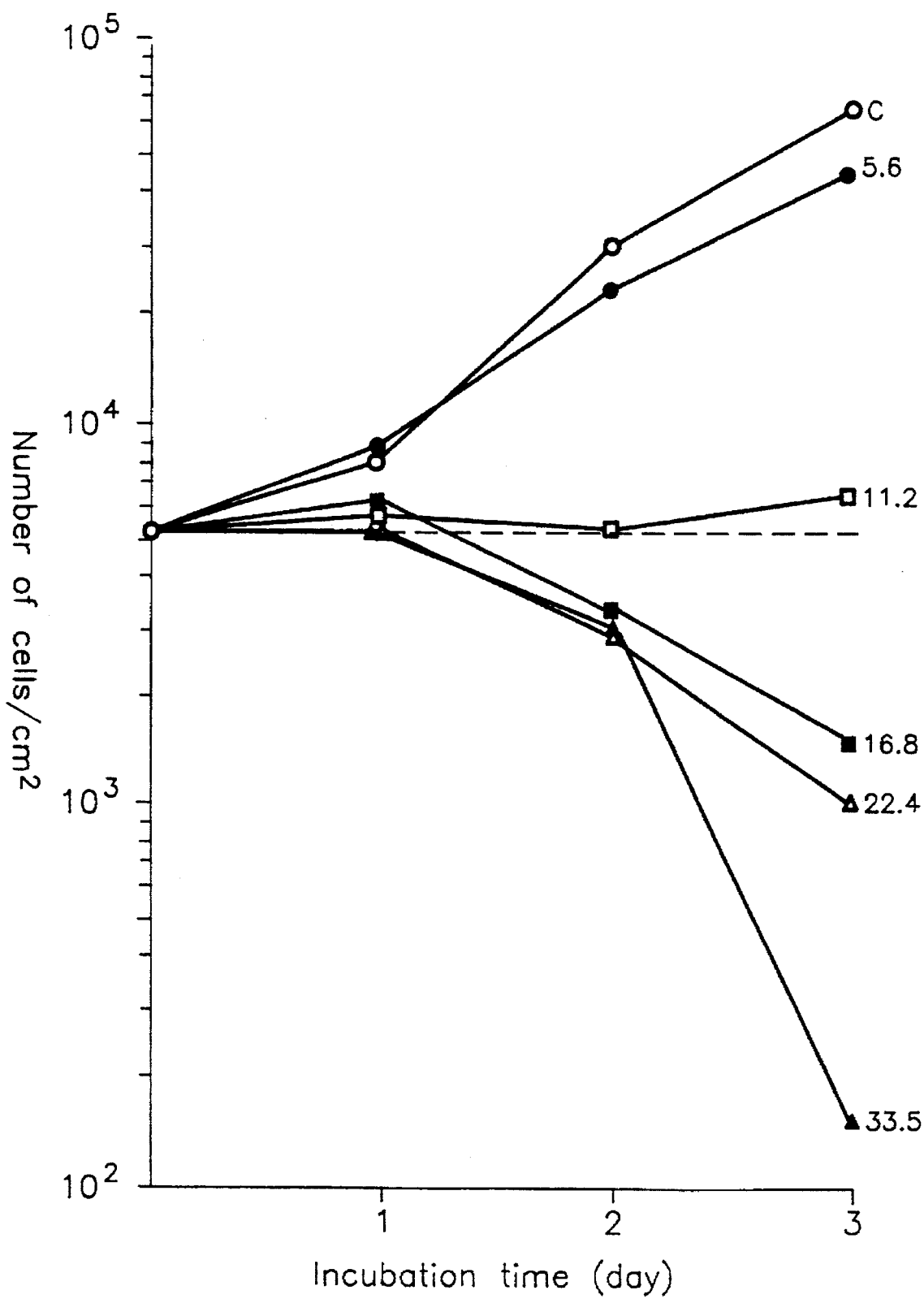
FIG. 10 shows the growth inhibitory and lethal effects of NFD on mouse melanoma B16 (M4) cells.

In FIG. 10, the concentrations of NFD in the medium are: o—o: NFD-free control (C); ●—●: 5.6 ng/ml; □—□: 11.2 ng/ml; ■—■: 16.8 ng/ml; ∆—∆: 22.4 ng/ml; ▲—▲: 33.5 ng/ml.

As shown in FIG. 10, NFD was found to inhibit the growth of mouse melanoma cells almost completely at 11.2 ng/ml and to cause necrosis in almost all tumor cells at 16.8–33.5 ng/ml.

Figure 11:
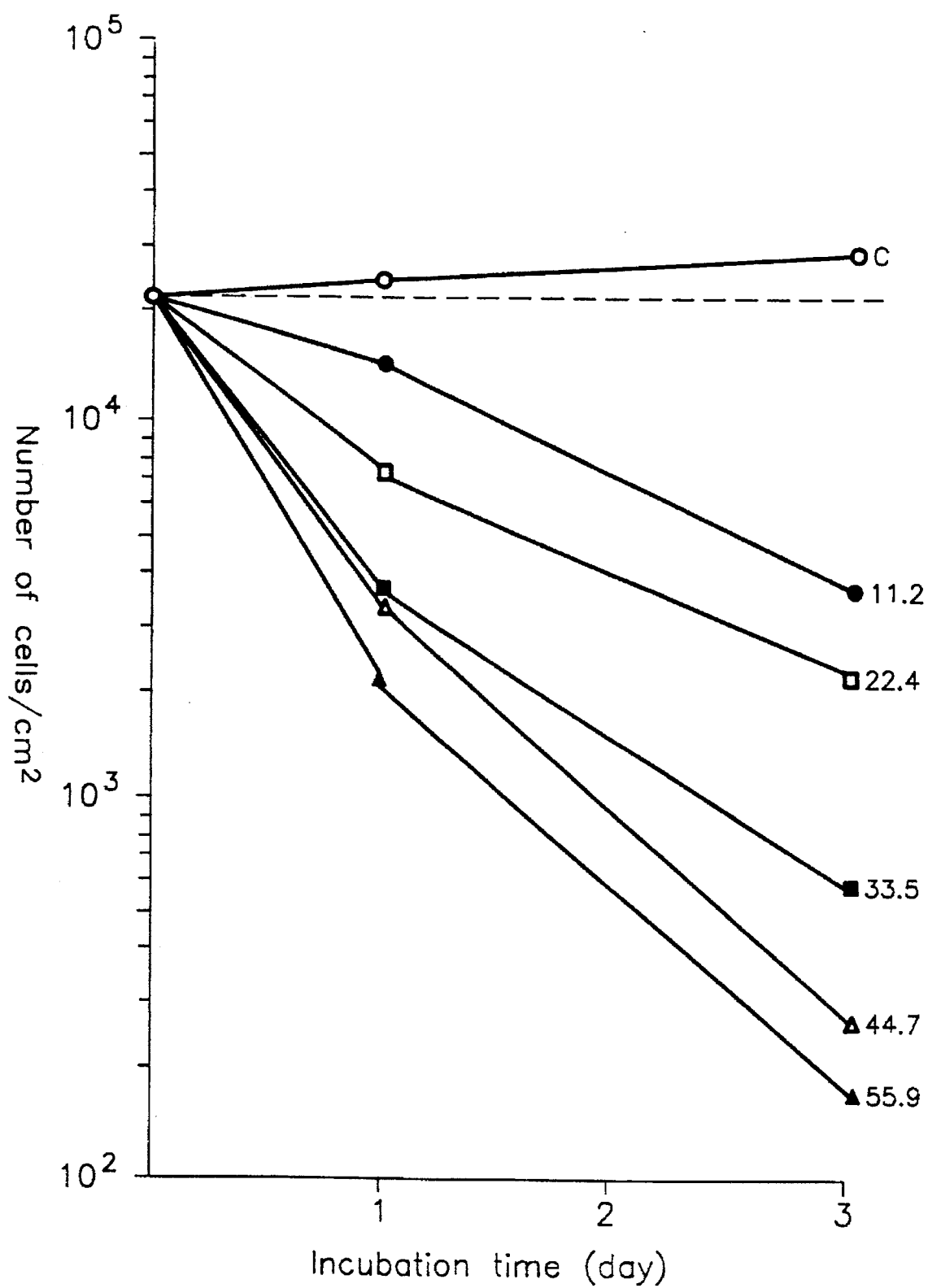
FIG. 11 shows the growth inhibitory and lethal effects of NFD on human malignant B-cell lymphoma cells.

In FIG. 11, the concentrations of NFD in the medium are: ○—○: NFD-free control (C); ●—●: 11.2 ng/ml; □—□: 22.4 ng/ml; ■—■: 33.5 ng/ml; △—△: 44.7 ng/ml; ▲—▲: 55.9 ng/ml.

As shown in FIG. 11, NFD was found to cause necrosis in human malignant B-cell lymphoma cells at 11.2–55.9 ng/ml.

Figure 12:
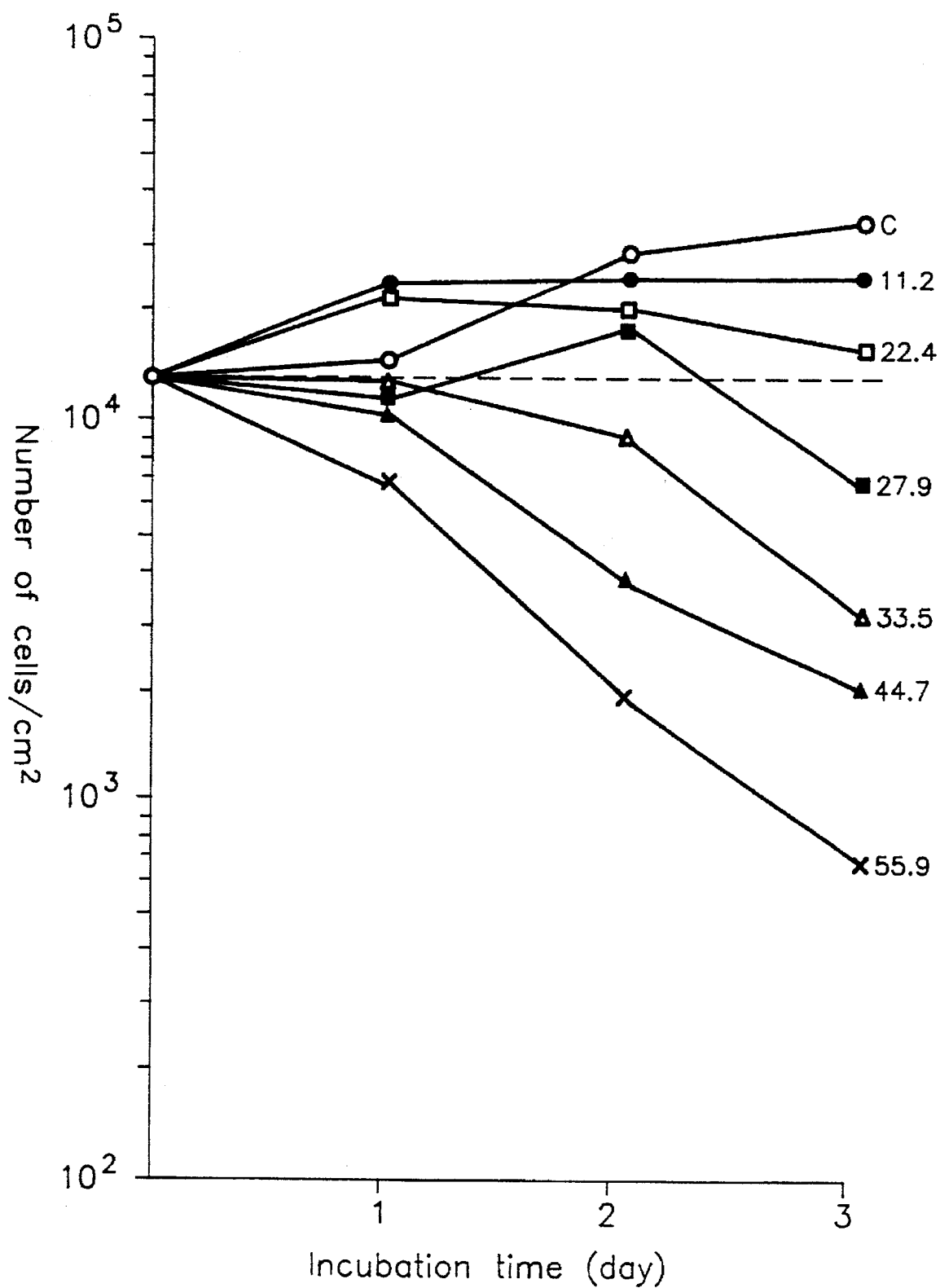
FIG. 12 shows the growth inhibitory and lethal effects of NFD on human chronic myelogenous leukemia K-562 cells.

In FIG. 12, the concentrations of NFD in the medium are: ○—○: NFD-free control (C); ●—●: 11.2 ng/ml; □—□: 22.4 ng/ml; ■—■: 27.9 ng/ml; △—△: 33.5 ng/ml; ▲—▲: 44.7 ng/ml; x—x: 55.9 ng/ml.

As shown in FIG. 12, NFD was found to inhibit the growth of human chronic myelogenous leukemia cells at 11.2–22.4 ng/ml and to cause necrosis in these tumor cells at 27.9–55.9 ng/ml.

Figure 13:
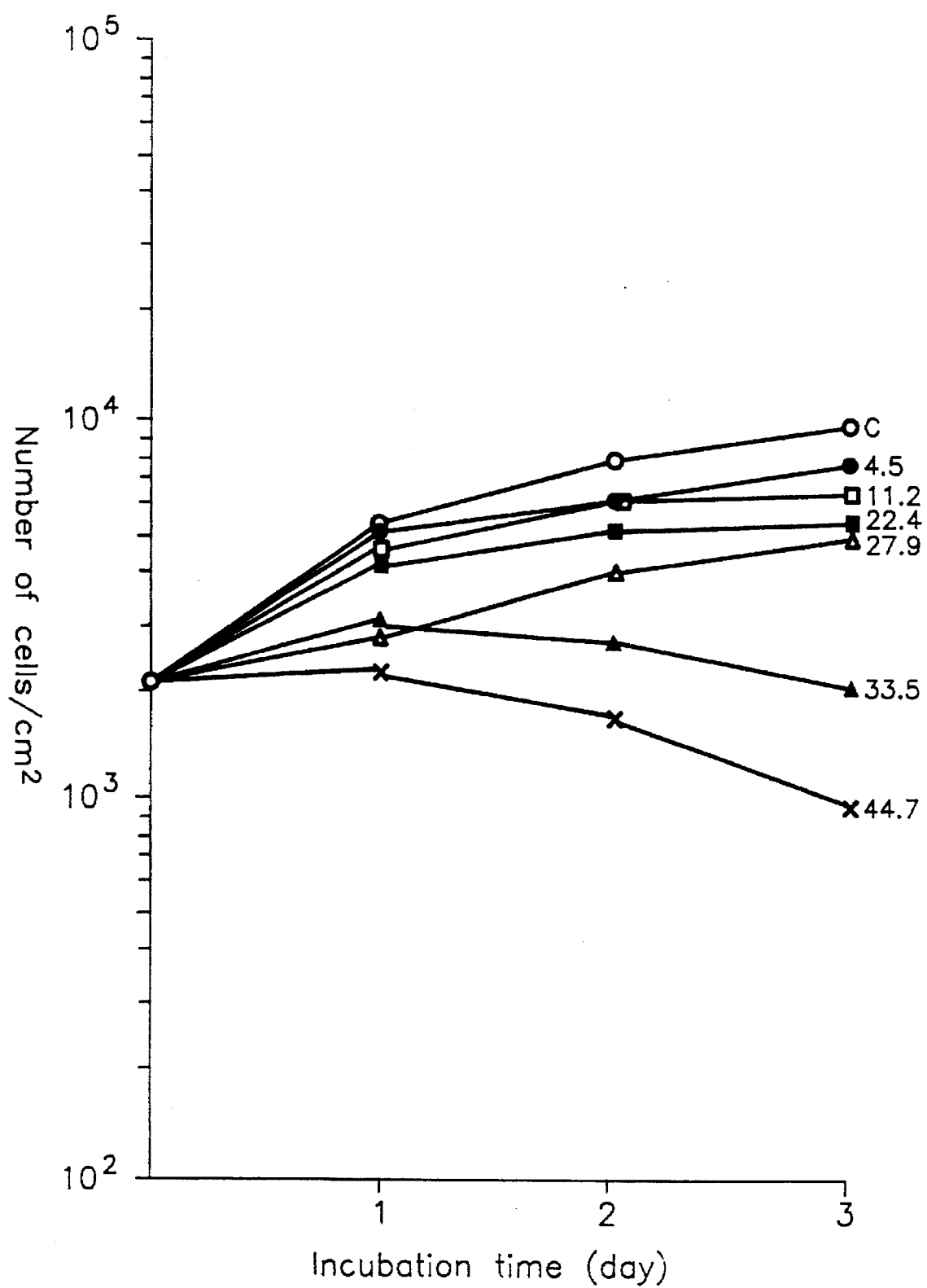
FIG. 13 shows the growth inhibitory and lethal effects of NFD on human pancreatic carcinoma ASPC-1 cells.

In FIG. 13, the concentrations of NFD in the medium are: ○—○: NFD-free control (C); ●—●: 5.6 ng/ml; □—□: 11.2 ng/ml; ■—■: 22.4 ng/ml; △—△: 27.9 ng/ml; ▲—▲: 33.5 ng/ml; x—x: 44.7 ng/ml.

As shown in FIG. 13, NFD was found to inhibit the growth of human pancreatic carcinoma cells almost completely at 33.5 ng/ml and to cause necrosis in these tumor cells at 44.7 ng/ml.

Figure 14:
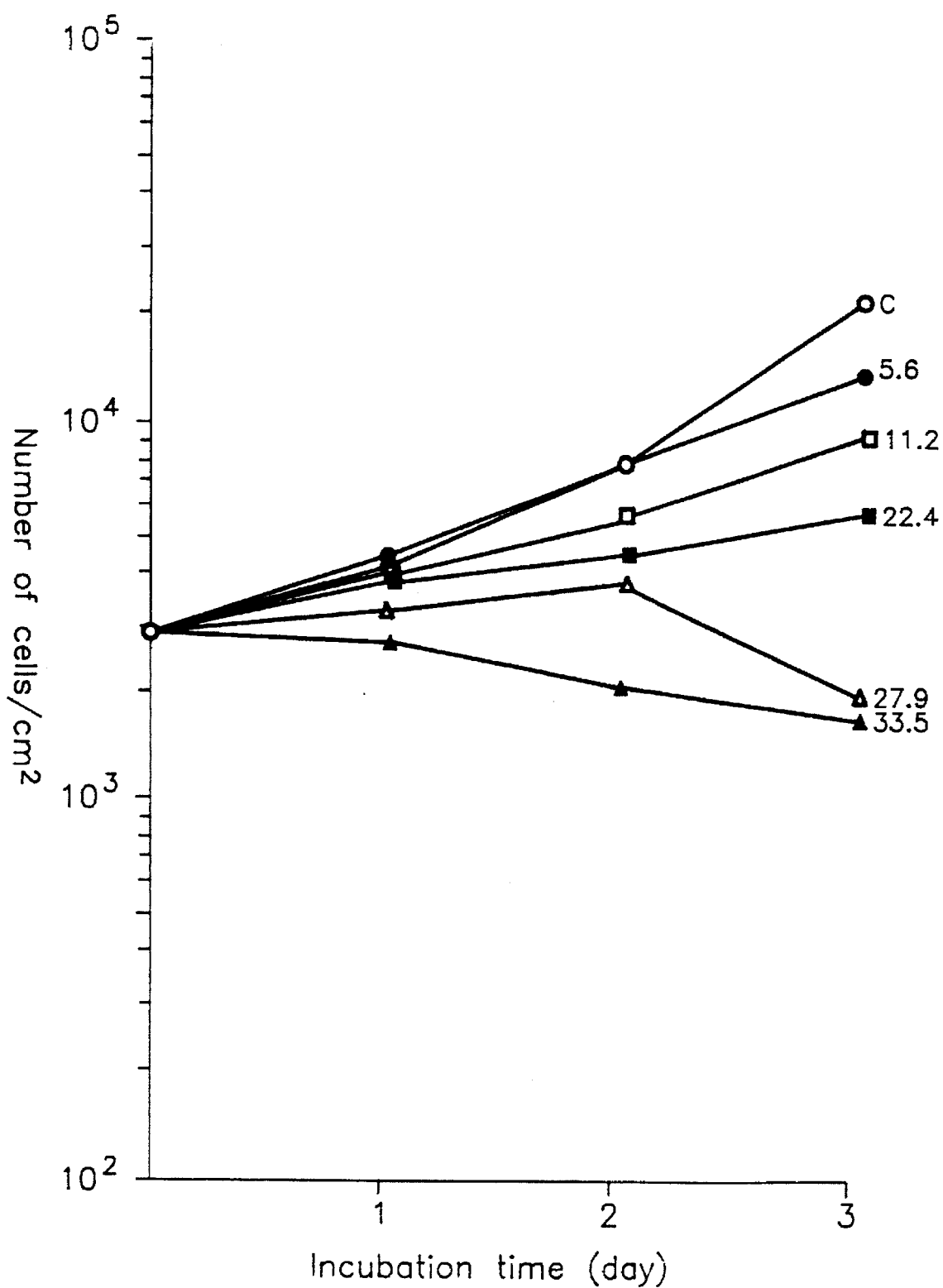
FIG. 14 shows the growth inhibitory and lethal effects of NFD on human neuroblastoma IMR-132 cells.

In FIG. 14, the concentrations of NFD in the medium are: ○—○: NFD-free control (C); ●—●: 5.6 ng/ml; □—□: 16.8 ng/ml; ■—■: 27.9 ng/ml; △—△: 44.7 ng/ml; ▲—▲: 55.9 ng/ml.

Figure 15:
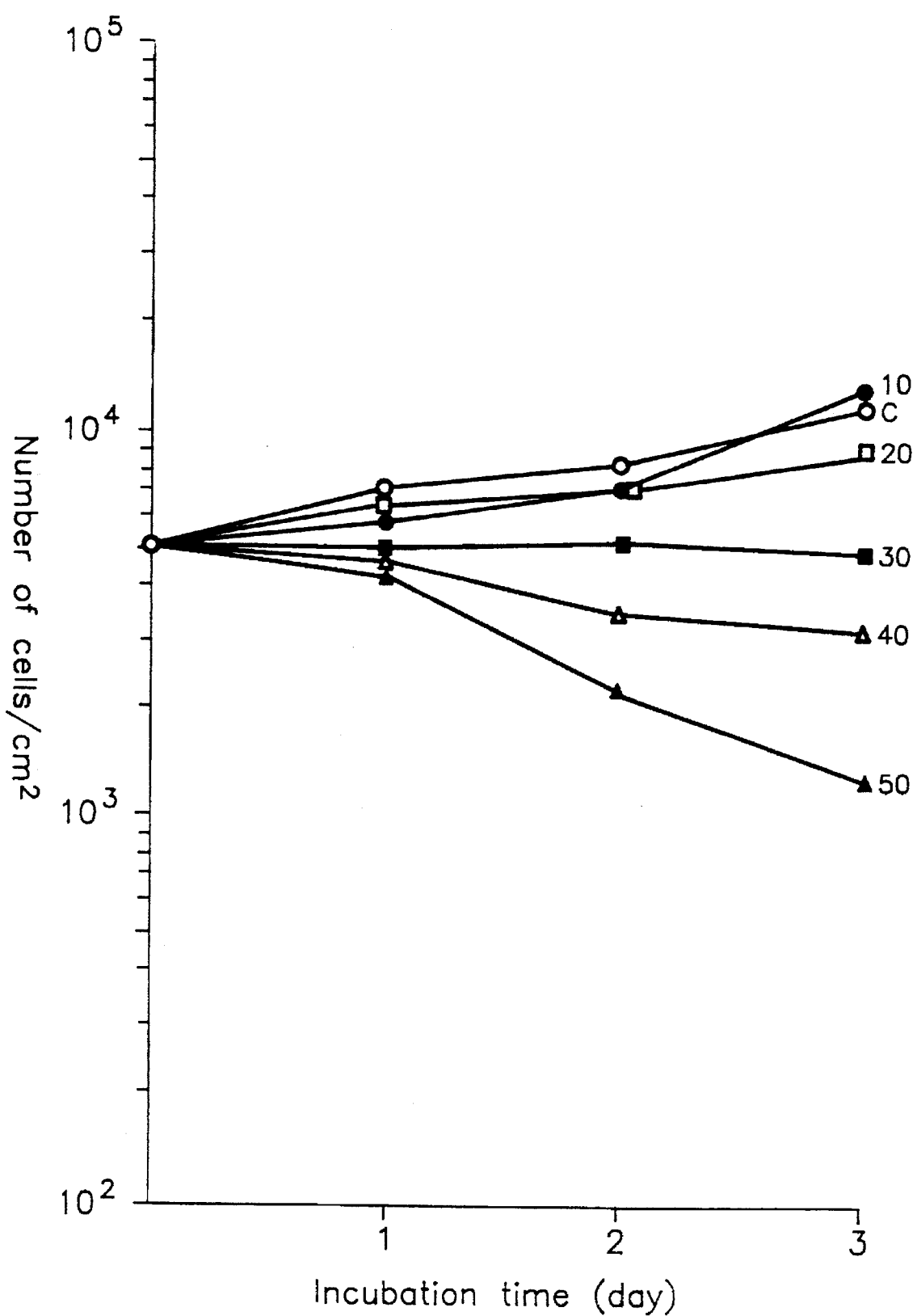
FIG. 15 shows the growth inhibitory and lethal effects of NFD on human lung small cell carcinoma SCCH-194 cells.

As shown in FIG. 14, NFD was found to inhibit the growth of human neuroblastoma cells almost completely at 44.7 ng/ml and to cause necrosis in these tumor cells at 55.9 ng/ml.

in FIG. 15, the concentrations of NFD in the medium are: ○—○: NFD-free control (C); ●—●: 10 ng/mi; □—□: 20 ng/ml; ■—■: 30 ng/ml; △—△: 40 ng/ml; ▲—▲: 50 ng/ml.

As shown in FIG. 15, NFD was found to inhibit the growth of human lung small cell carcinoma cells almost completely at 30 ng/ml and to cause necrosis in these tumor cells at 40–60 ng/ml.

Figure 16:
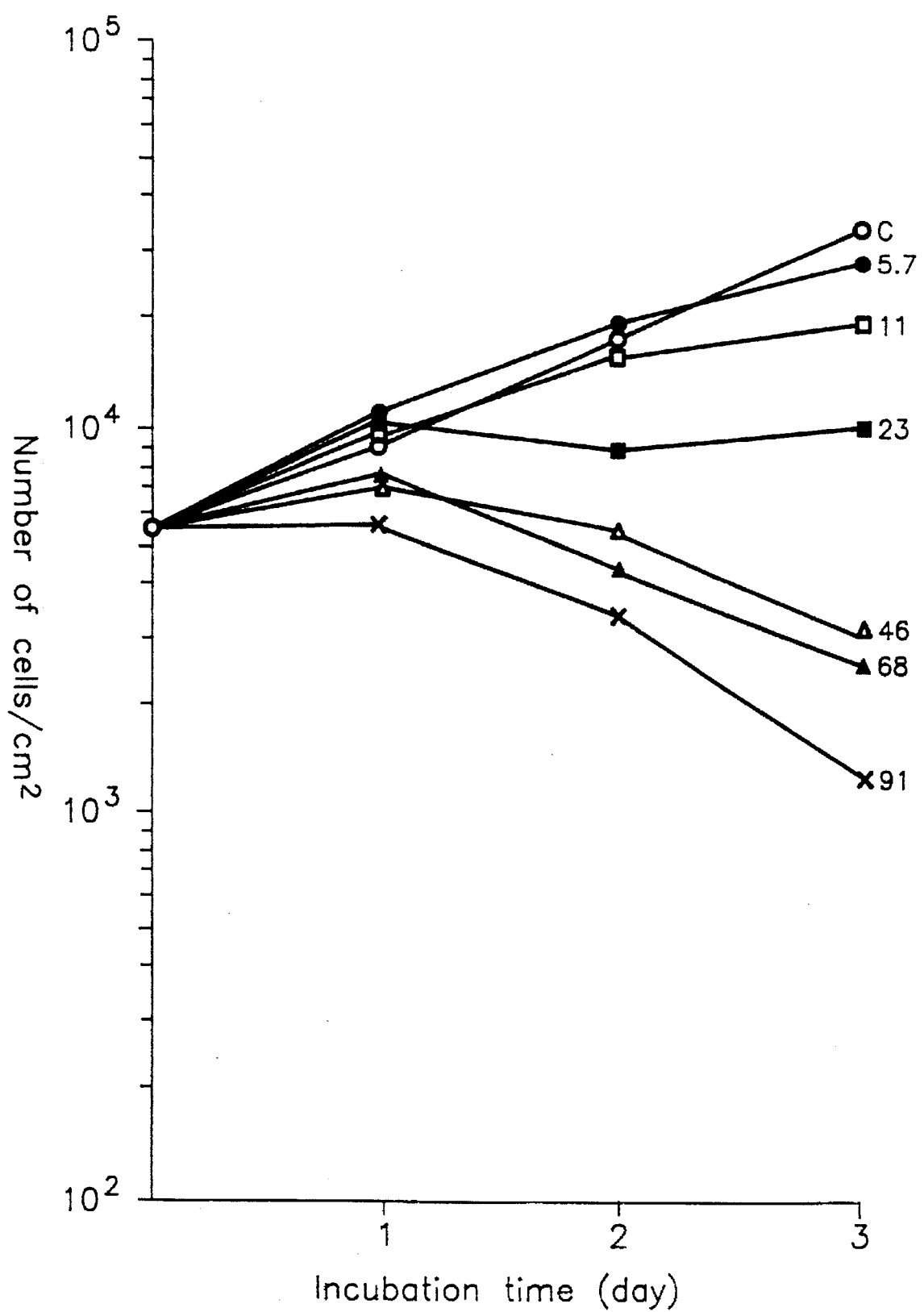
FIG. 16 shows the growth inhibitory and lethal effects of NFD on human urinary bladder carcinoma T24 cells.

In FIG. 16, the concentrations of NFD in the medium are: ○—○: NFD-free control (C); ●—●: 5.7 ng/ml; □—□: 11 ng/ml; ■—■: 23 ng/ml; △—△: 46 ng/ml; ▲—▲: 68 ng/ml.

As shown in FIG. 16, NFD was found to inhibit the growth of human uninary bladder carcinoma cells almost completely at 23 ng/ml and to cause necrosis in these tumor cells at 46 ng/ml.

Figure 17:
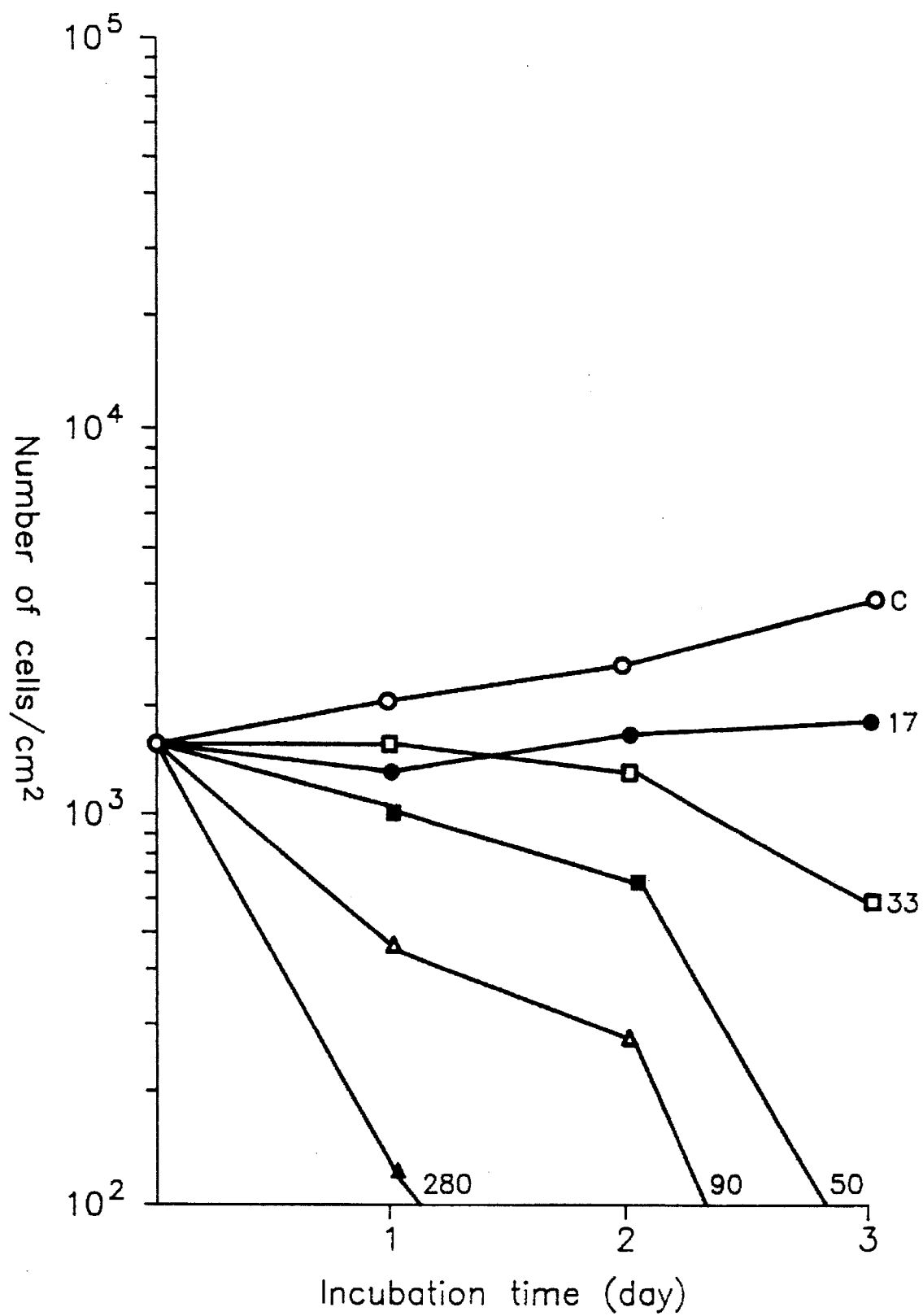
FIG. 17 shows the growth inhibitory and lethal effects of NFD on human renal cell carcinoma VMRC-RCW cells.

In FIG. 17, the concentrations of NFD in the medium are: ○—○: NFD-free control (C); ●—●: 17 ng/ml; □—□: 33 ng/ml; ■—■: 50 ng/ml; △—△: 90 ng/ml; ▲—▲: 280 ng/ml.

As shown in FIG. 17, NFD was found to inhibit the growth of human renal cell carcinoma cells almost completely at 17 ng/ml and to cause necrosis in almost all tumor cells at 50 ng/ml.

Figure 18:
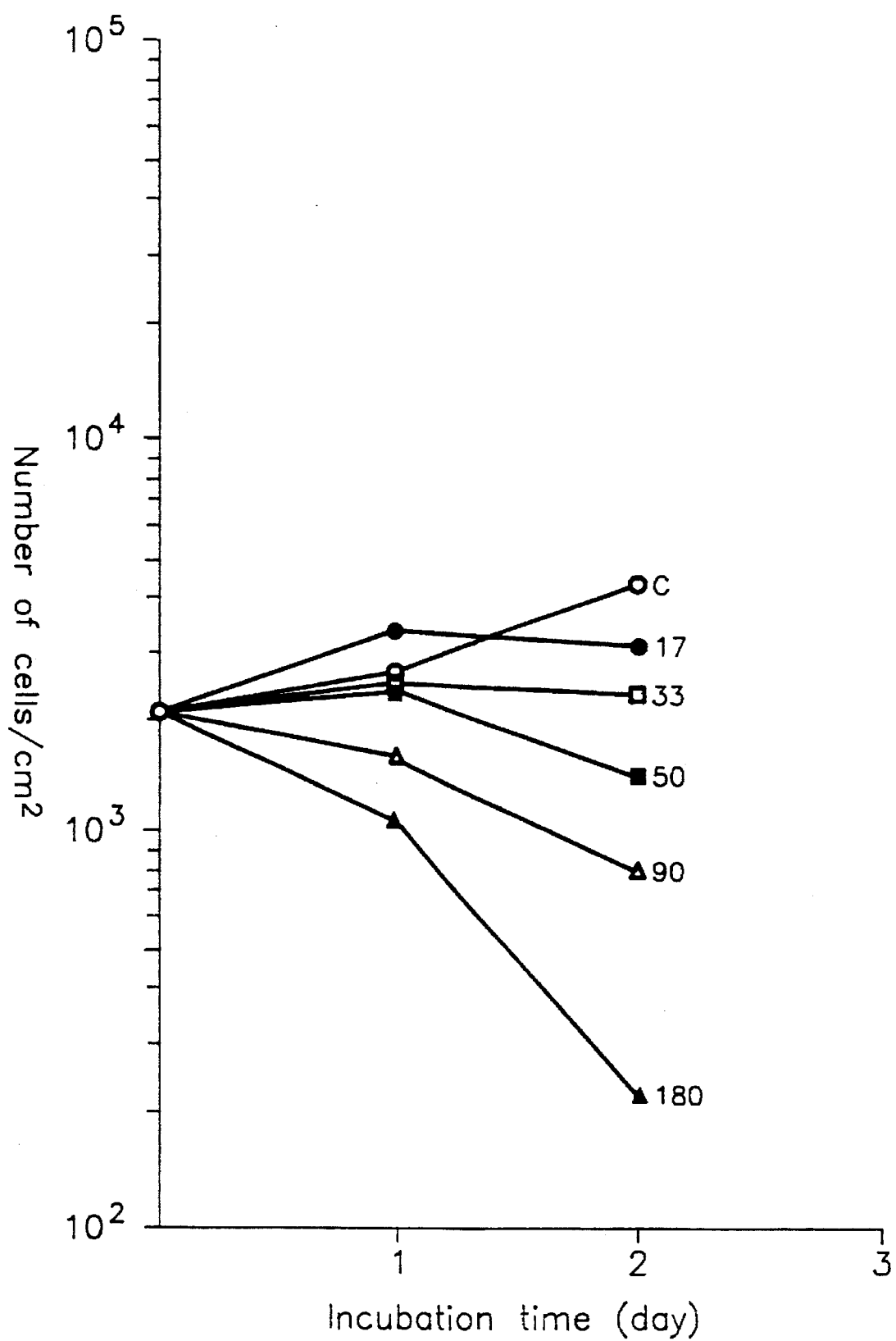
FIG. 18 shows the growth inhibitory and lethal effects of NFD on human gastric cancer NUGC-2 cells.

In FIG. 18, the concentrations of NFD in the medium are: ○—○: NFD-free control (C); ●—●: 17 ng/ml; □—□: 33 ng/ml; ■—■: 50 ng/ml; △—△: 90 ng/ml; ▲—▲: 170 ng/ml.

As shown in FIG. 18, NFD was found to inhibit human gastric cancer cells almost completely at 33 ng/ml and to cause necrosis in these tumor cells at 50 ng/ml.

Figure 19:
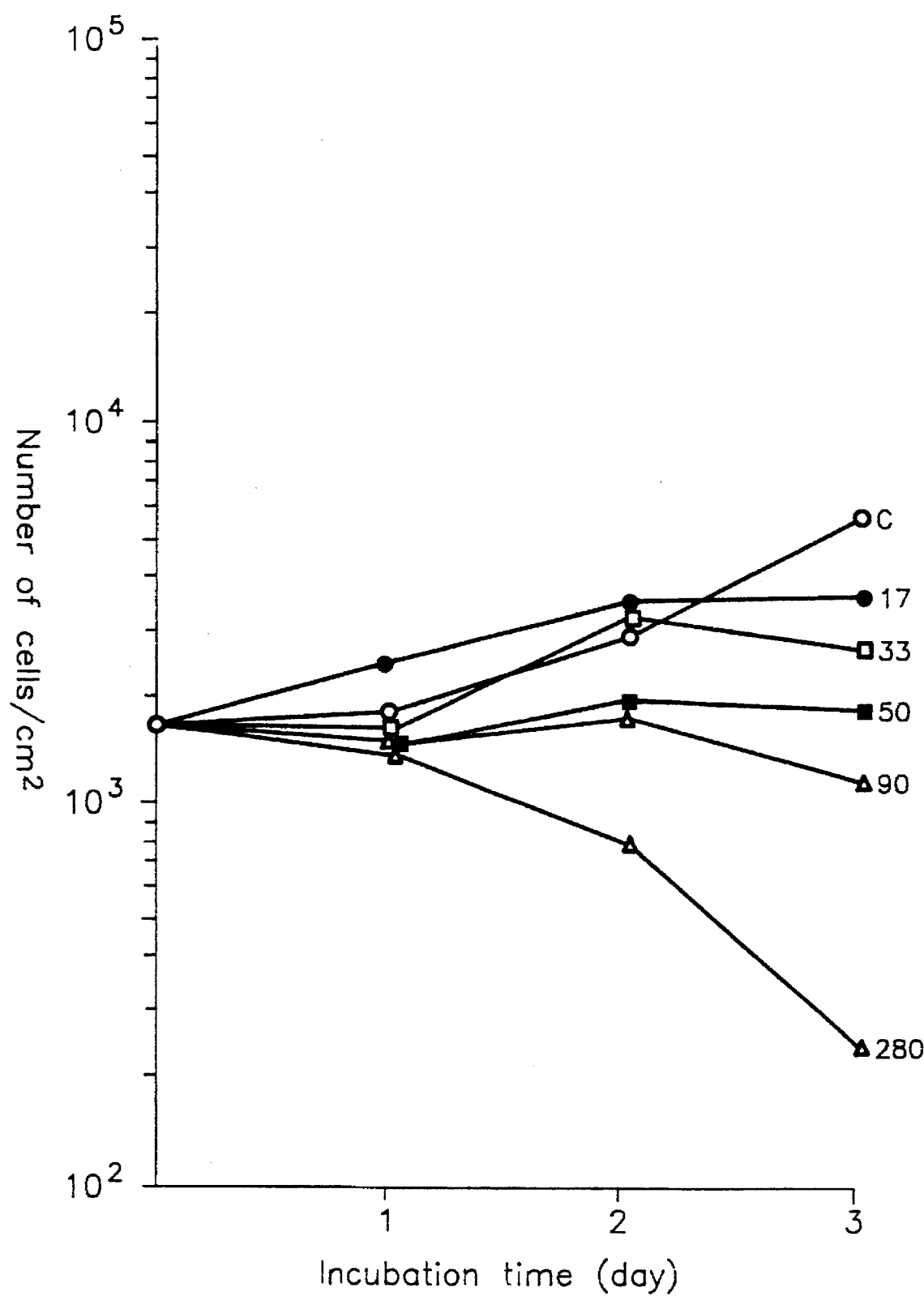
FIG. 19 shows the growth inhibitory and lethal effects of NFD on human thyroid carcinoma 8305C cells.

In FIG. 19, the concentrations of NFD in the medium are: ○—○: NFD-free control (C); ●—●: 17 ng/ml; □—□: 33 ng/ml; ■—■: 50 ng/ml; △—△: 90 ng/ml; ▲—▲: 280ng/ml.

As shown in FIG. 19, NFD was found to inhibit the growth of human thyroid carcinoma cells almost completely at 28 ng/ml and to cause necrosis in these tumor cells at 51 ng/ml.

Figure 20:
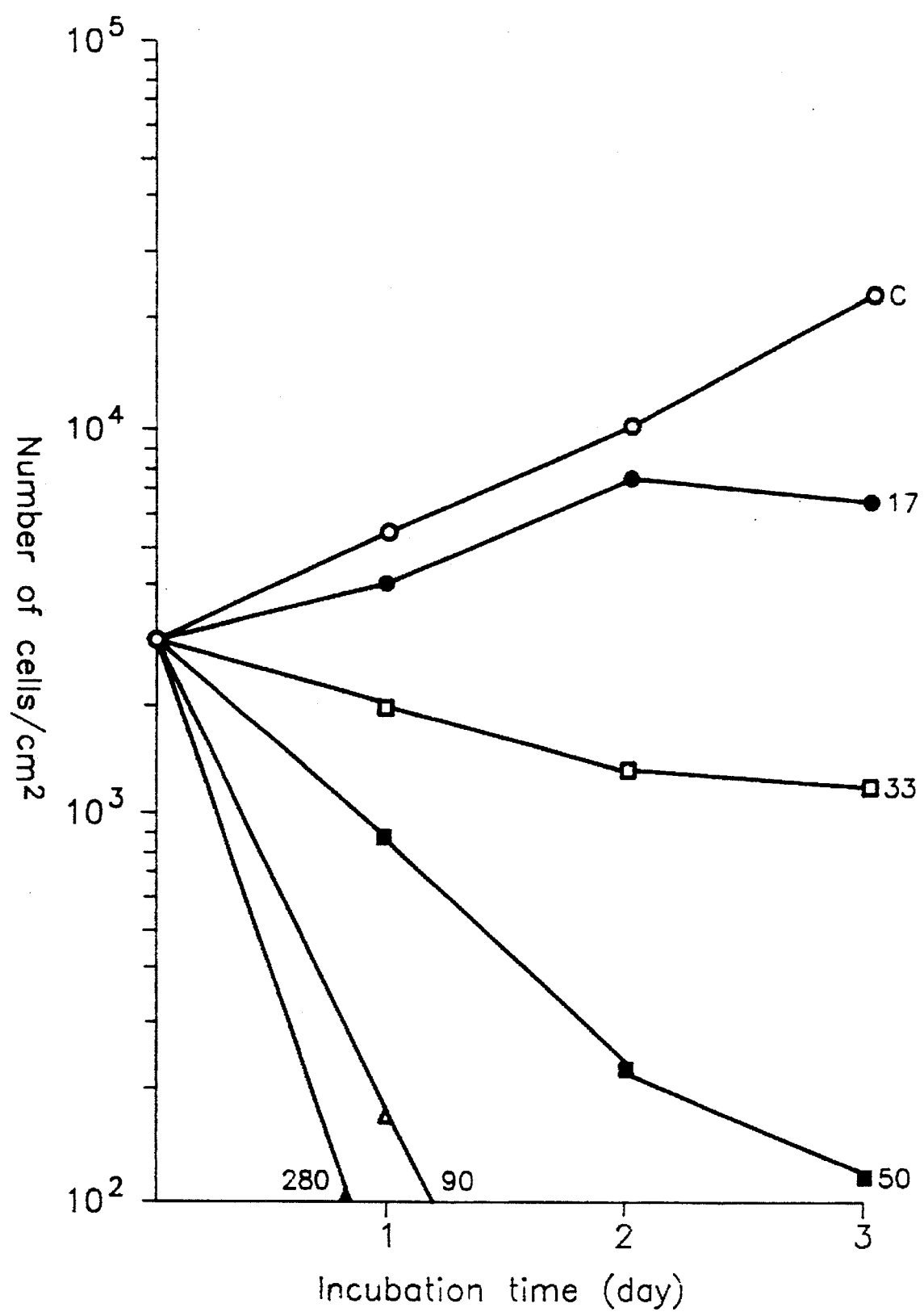
FIG. 20 shows the growth inhibitory and lethal effects of NFD on human breast cancer MRK-nu-1 cells.

In FIG. 20, the concentrations of NFD in the medium are: ○—○: NFD-free control (C); ●—●: 17 ng/ml; □—□: 33 ng/ml; ■—■: 50 ng/ml; △—△: 90 ng/ml; ▲—▲: 280 ng/ml.

As shown in FIG. 20, NFD was found to inhibit the growth of human breast cancer cells almost completely at 33 ng/ml and to cause necrosis in these tumor cells at 50 ng/ml or above.

Figure 21:
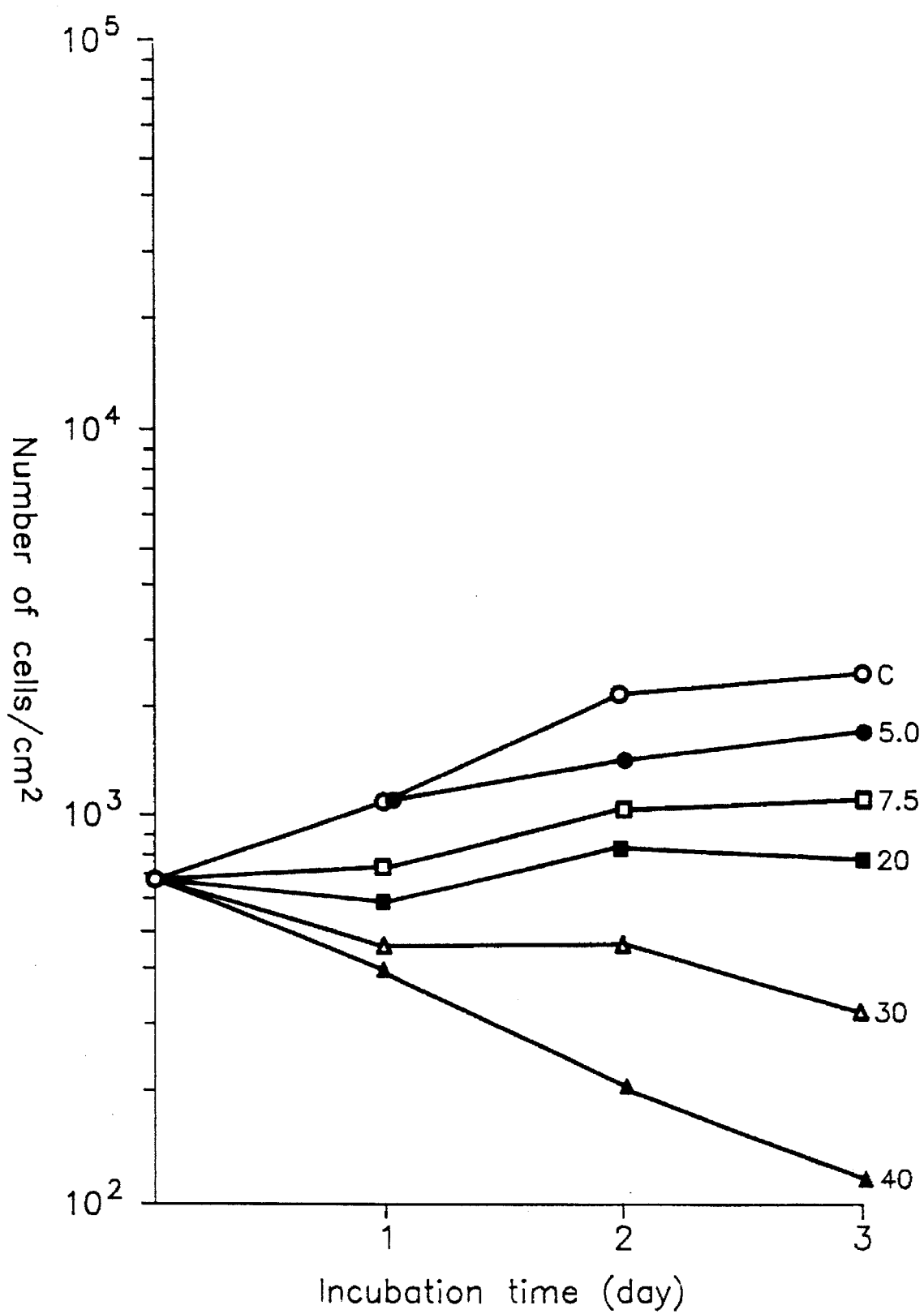
FIG. 21 shows the growth inhibitory and lethal effects of NFD on human hepatoma HUH-7 cells.

In FIG. 21, the concentrations of NFD in the medium are: ○—○: NFD-free control (C); ●—●: 5.0 ng/ml; □—□: 7.5 ng/ml; ▲—▲: 20 ng/ml; △—△30 ng/ml; ▲—▲: 40 ng/ml.

As shown in FIG. 21, NFD was found to inhibit the growth of human hepatoma cells almost completely at 20 ng/ml and to cause necrosis in these tumor cells at 30 ng/ml or above.

Figure 22:
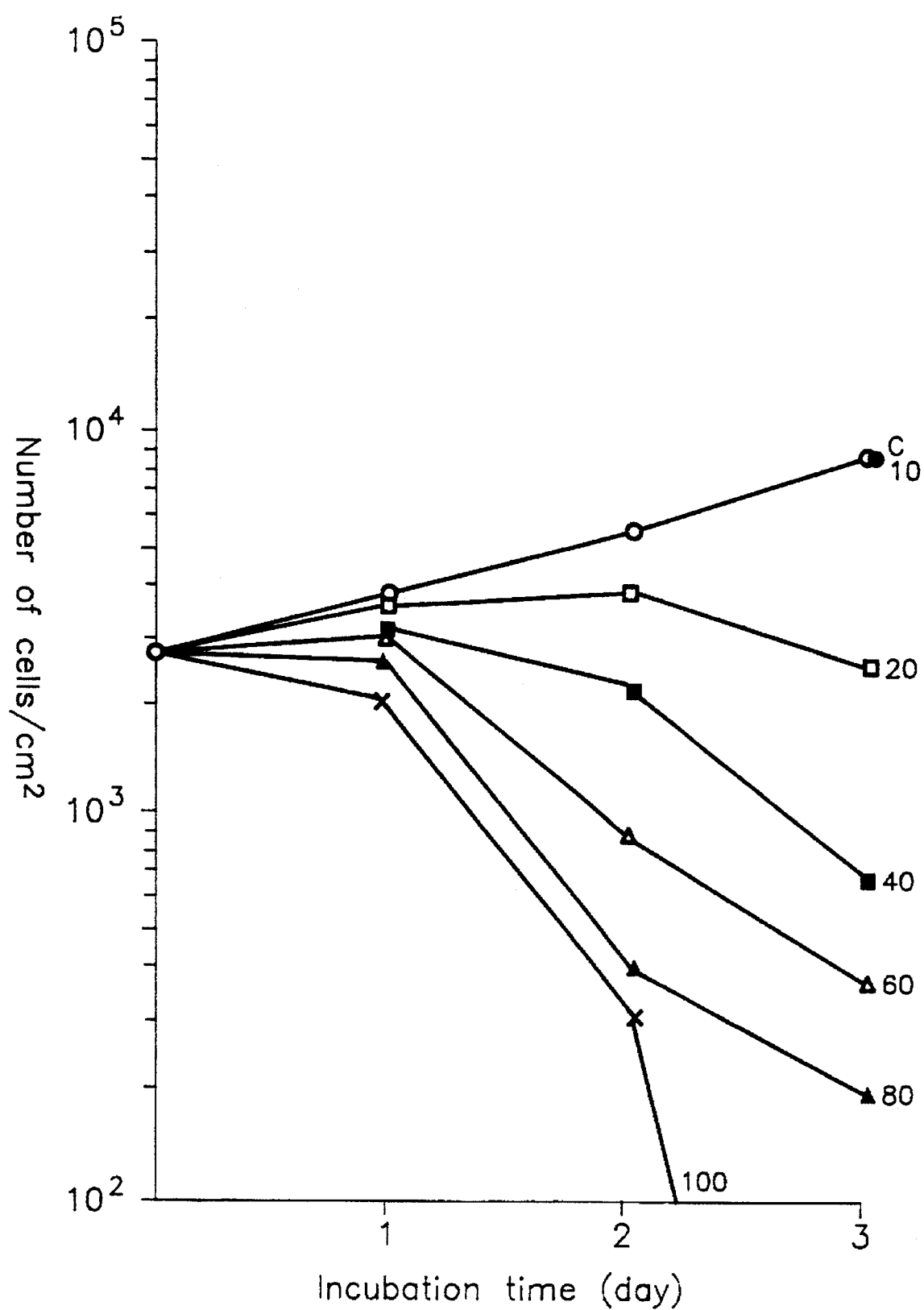
FIG. 22 shows the growth inhibitory and lethal effects of NFD on human ovarian carcinoma TYK-nu cells.

In FIG. 22, the concentrations of NFD in the medium are: ○—○: NFD-free control (C); ●—●: 10 ng/ml; □—□: 20 ng/ml; ■—■: 40 ng/ml; △—△: 60 ng/ml; ▲—▲: 80 ng/ml.

As shown in FIG. 22, NFD was found to inhibit the growth of human ovarian carcinoma cells almost completely at 20 ng/ml and to cause necrosis in almost all tumor cells at 40 ng/ml or above.

Figure 23:
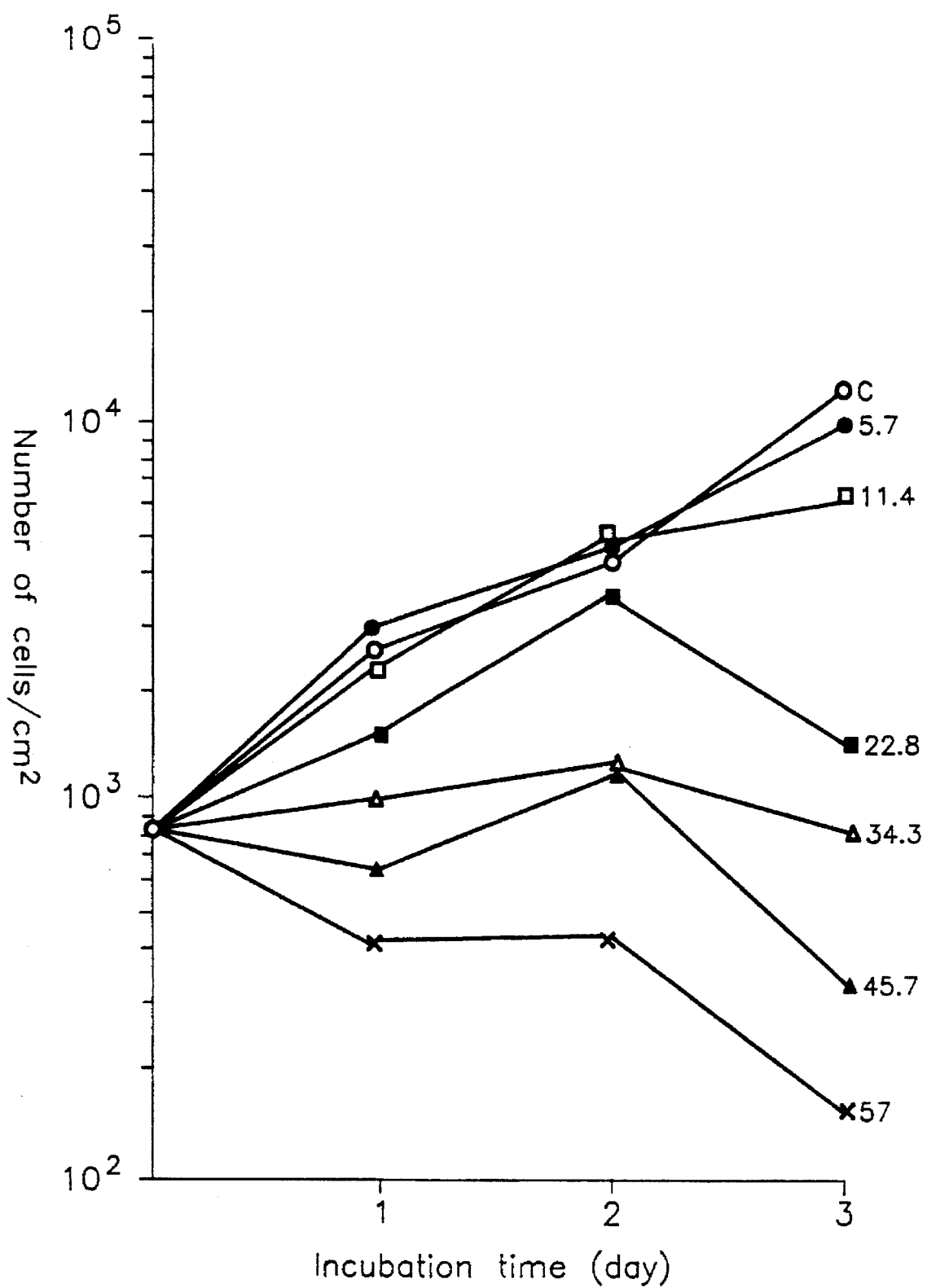
FIG. 23 shows the growth inhibitory and lethal effects of NFD on human chorio carcinoma BeWo cells.

In FIG. 23, the concentrations of NFD in the medium are: ○—○: NFD-free control (C); ●—●: 5.7 ng/ml; □—□: 11.4 ng/ml; ■—■: 22.8 ng/ml; △—△: 34.3 ng/ml; ▲—▲: 45.7 ng/ml.

As shown in FIG. 23, NFD was found to inhibit the growth of human chorio carcinoma cells almost completely at 34.3 ng/ml and to cause necrosis in these tumor cells at 45.7 ng/ml.

Figure 24:
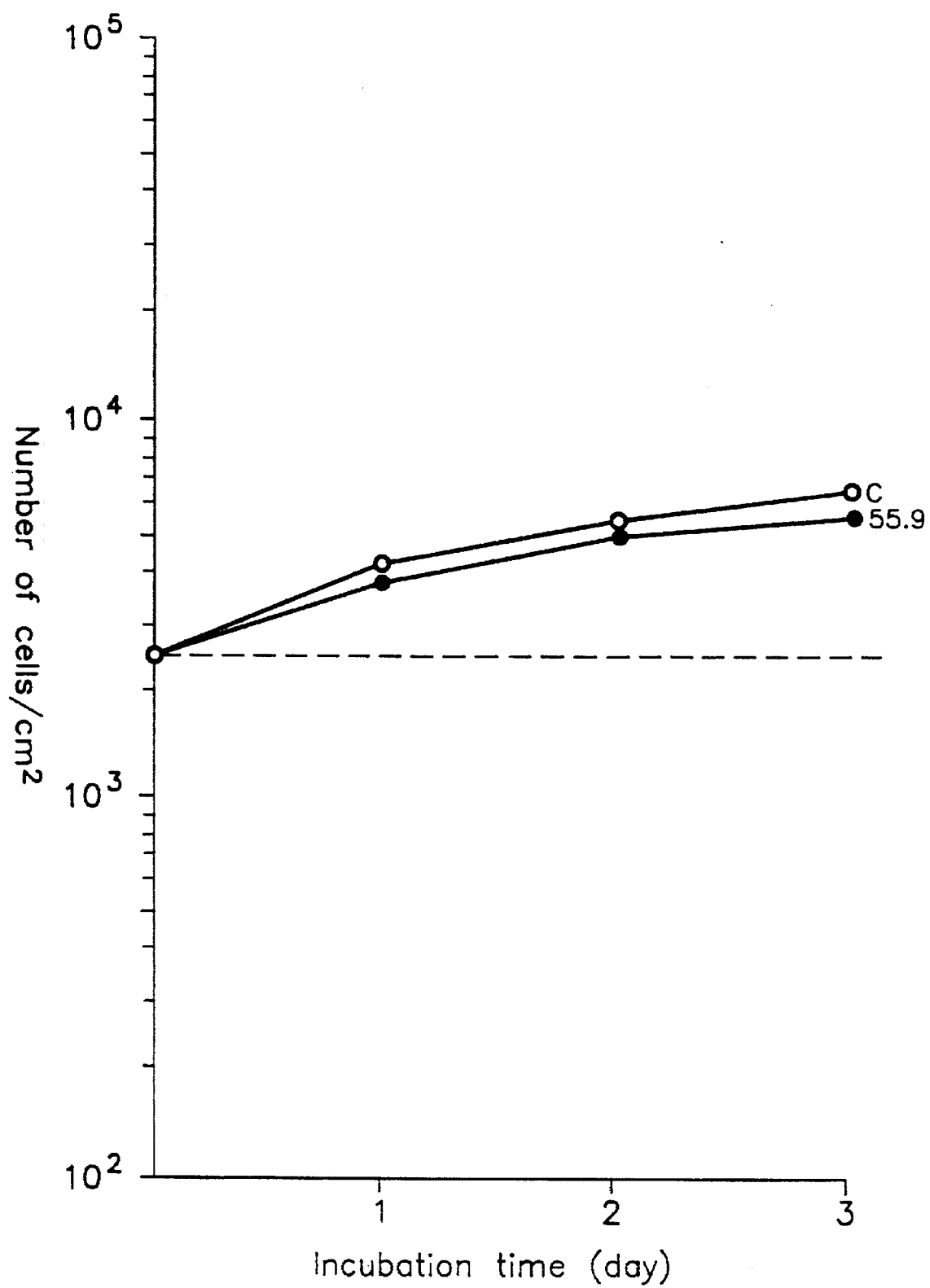
FIG. 24 shows the growth inhibitory and lethal effects of NFD on normal human N6KA fibroblasts.

In FIG. 24, the concentrations of NFD in the medium are: ○—○: NFD-free control (C); ●—●: 55.9 ng/ml.

Figure 25:
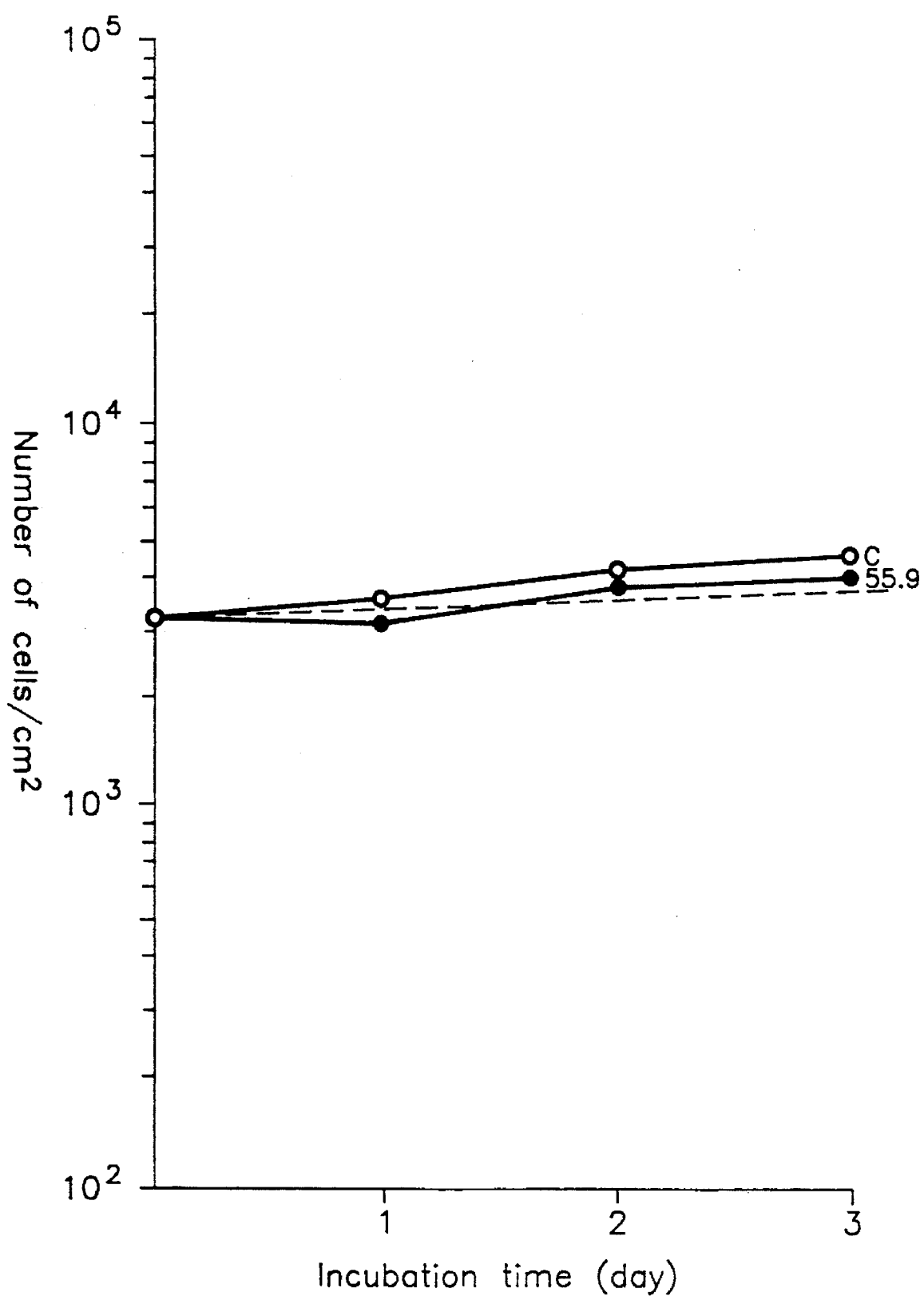
FIG. 25 shows the growth inhibitory and lethal effects of NFD on normal human tracheal epithelial cells.

In FIG. 25, the concentrations of NFD in the medium are: ○—○: NFD-free control (C); ●—●: 55.9 ng/ml.

Figure 26:
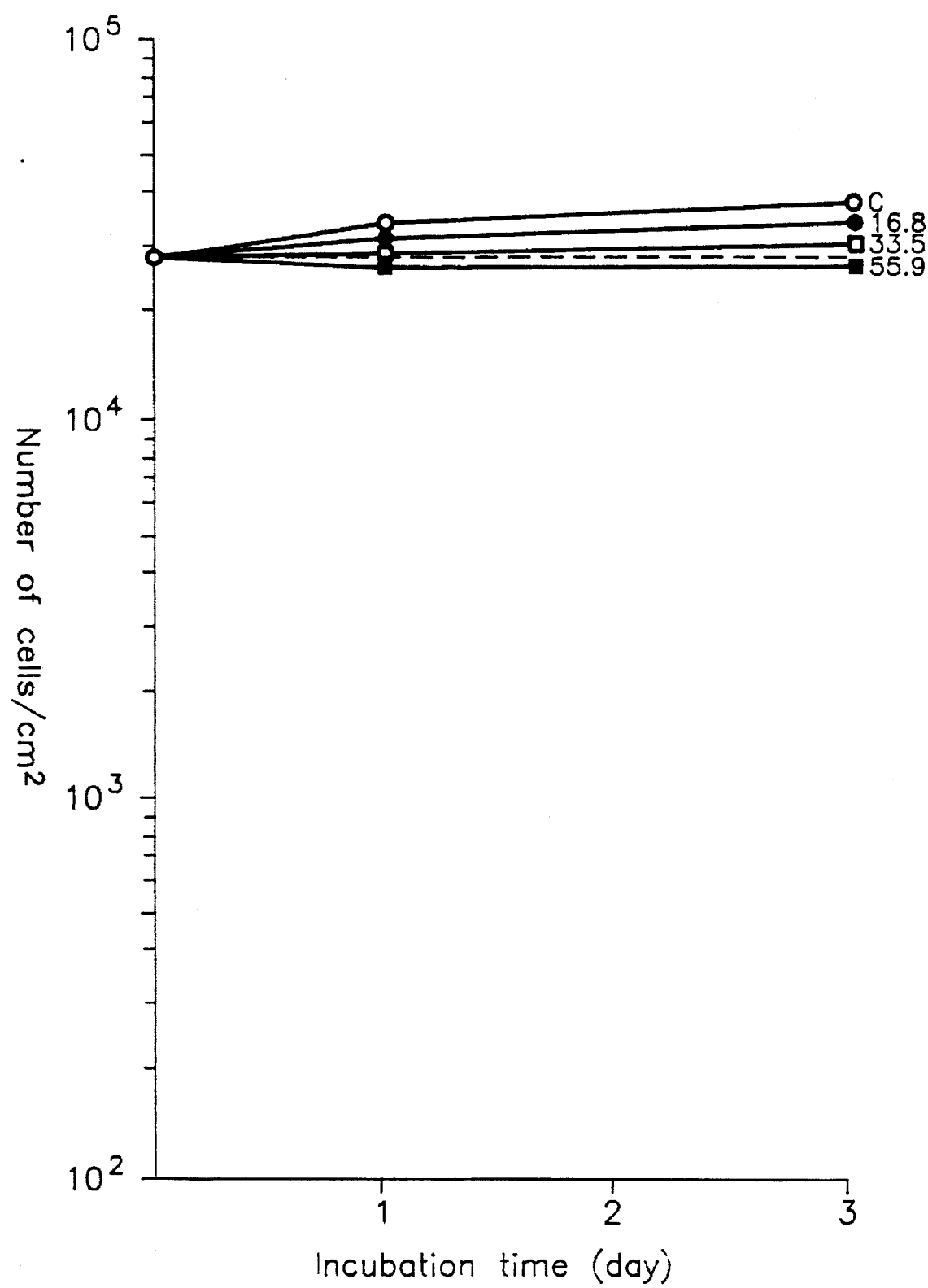
FIG. 26 shows the growth inhibitory and lethal effects of NFD on normal human peripheral blood lymphocytes.

In FIG. 26, the concentrations of NFD in the medium are: ○—○: NFD-free control (C); ●—●: 16.8 ng/ml; □—□: 33.5 ng/ml; ■—■: 55.9 ng/ml.

Figure 27:
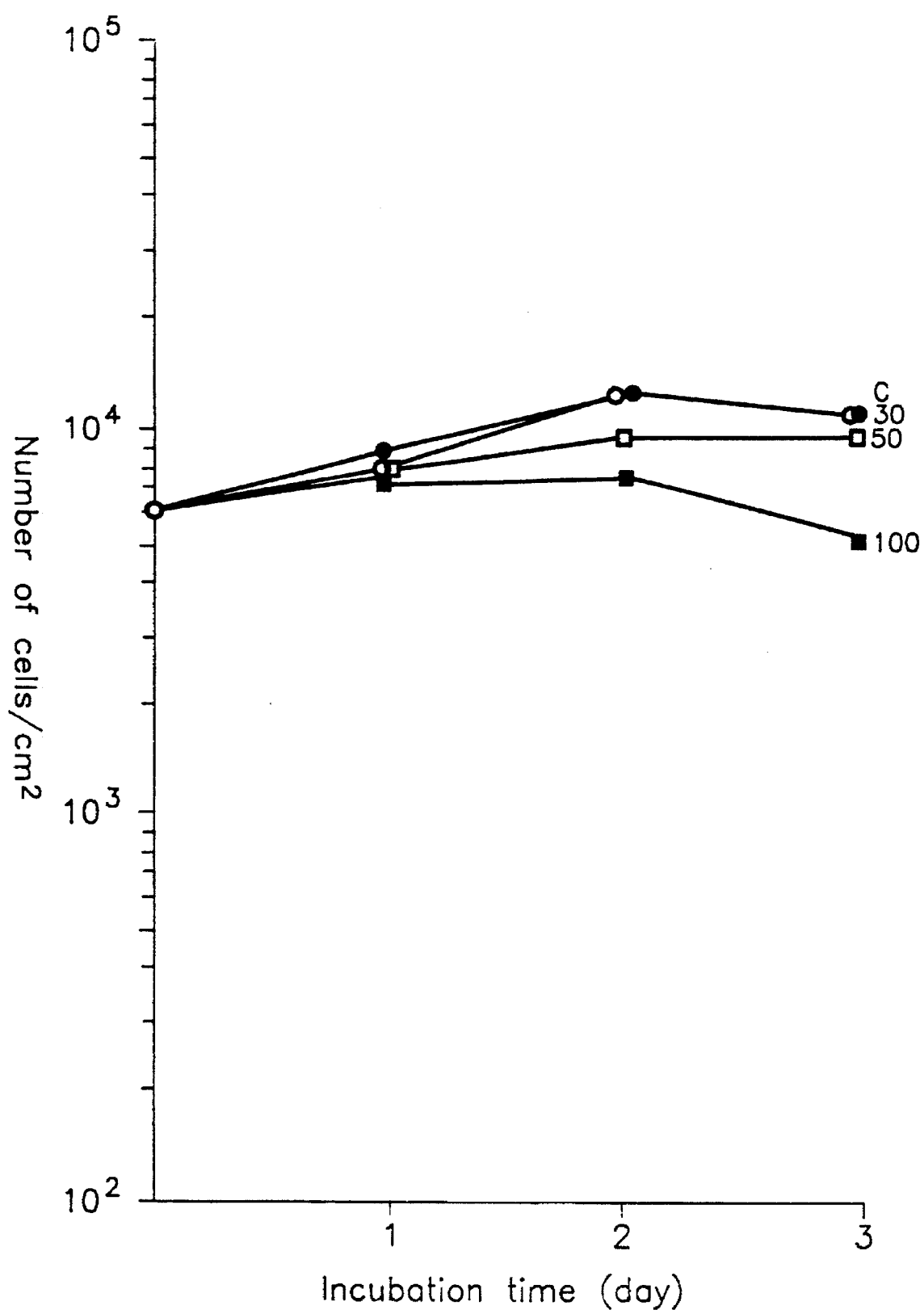
FIG. 27 shows the growth inhibitory and lethal effects of NFD on normal human renal cells.

In FIG. 27, the concentrations of HNFD in the medium are: ○—○: HNFD-free control (C); ●—●: 30 ng/ml; □—□: 50 ng/ml; ■—■: 100 ng/ml.

As shown in FIG. 27, NFD inhibited the growth of normal renal cells only at higher concentration of 100 ng/ml.

As shown in FIGS. 24, 25, 26 and 27, NFD was found to have no adverse effects on the growth of normal human fibroblasts, normal human tracheal epithelial cells, normal human peripheral lymphocytes or normal human renal cells at the concentrations which cause necrosis in the above tumor cells.

(6) 50% growth-inhibitorydose ($LD_{50}$, $IC_{50}$)

Table 1 summarizes the 50% growth-inhibitory dose ($LD_{50}$, $IC_{50}$) of NFD for each cell line, which was determined, based on FIGS. 1–12, from the viability of cells after exposure to NFD in the culture medium for three days, said viability being represented by the percentage of the number of living cells in the test wells with respect to the number of living cells in the control well (NFD-free medium).

[Table 1] 50% Growth-inhibitory doses (LD$_{50}$, IC$_{50}$) of NFD for human and mice malignant and normal cells

| Cell line | LD$_{50}$ (IC$_{50}$) (ng/ml) |
|---|---|
| Human lung adenocarcinoma A-549 cells | 9.5 |
| Human lung adenocarcinoma VMRC-LCD cells | 13 |
| Human lung adenocarcinoma SK-LU-1 cells | 17 |
| Human lung squamous cell carcinoma Calu-1 cells | 17 |
| Human colon adenocarcinoma WiDr cells | 11 |
| Human prostate cancer LNCaP cells | 1.7 |
| Human vaginal squamous cell carcinoma A-431 cells | 21 |
| Human cervical carcinoma HeLa cells | 18 |
| Human cholangiocarcinoma HuCC-T1 cells | 20 |
| Mouse melanoma B16 (M4) cells | 6.7 |
| Human malignant B-cell lymphoma cells | 5.6 |
| Human chronic myelogenous leukemia K562 cells | 14 |
| Human pancreatic carcinoma ASPC-1 cells | 17 |
| Human neuroblastoma IMR-132 cells | 10 |
| Human lung small cell carcinoma SCCH-194 cells | 10 |
| Human urinary bladder carcinoma T24 cells | 21 |
| Human renal cell carcinoma VMRC-RCW cells | 19 |
| Human gastric cancer NUGC-2 cells | 17 |
| Human thyroid carcinoma 8305C cells | 25 |
| Human breast cancer MRK-nu-1 cells | 12 |
| Human hepatoma HuH-7 cells | 5.5 |
| Human ovarian carcinoma TYK-nu cells | 17 |
| Human chorio carcinoma BeWo cells | 18 |
| Normal human N6KA fibroblasts | 84 |
| Normal human tracheal epithelial cells | >55 |
| Normal human peripheral blood lymphocytes | 84 |
| Normal human renal cells | 65 |

The LD$_{50}$ values of NFD were found to be within 5.5–25 ng/ml for all malignant tumor cells and hematologic neoplasms.

The LD$_{50}$ values of NFD for normal human cells after three days of exposure in the culture medium, which were calculated based on FIGS. 13–15, are also presented in Table 1. The LD$_{50}$ values range within 55–84 ng/ml.

EXAMPLE 3

Inhibition of Two-step Carcinogenesis in Mouse Lungs

Female ICR mice were used as test animals. Fifteen mice were housed in a cage and provided with the pellet diet and drinking water ad libitum. After one week of preliminary rearing, the six-week-old mice were given in the back a subcutaneous injection of 10 mg/kg body weight of 4-nitroquinoline-N-oxide (4NQO) dissolved in a mixture of olive oil and cholesterol (20:1). From five weeks after initiation, the mice were allowed to orally take 8% glycerol ad libitum as a carcinogenic promoter. The mice which received 4 NQO and 8% glycerol for 25 weeks served as a positive control. On the other hand, the mice in the test group were given ad libitum 8% glycerol containing 0.1 ng/ml of NFD for 25 weeks. Thirty weeks after the onset of the experiment, the mice were killed by cervical dislocation, and the lungs were removed after fixation with formalin under autopsy. Under a stereomicroscope, the adenomas formed in the lung were observed, and the number of adenomas was determined. The numbers were compared between the positive control and NFD-administered groups. Table 2 summarizes the experimental results. Table 2 shows that the expression percentage of lung adenomas in the NFD group, wherein NFD was administered 30th week after onset of the experiment, was ⅓ lower than that in the positive control group, which indicates the significant inhibition of adenoma formation in the lung.

TABLE 2

Number and expression percentage of lung adenomas in mice

| Group | Total number of adenomas | Number of adenomas/ mouse | Percentage of mice having adenomas |
|---|---|---|---|
| I Water alone as drinking water | 0 | 0 | 0 |
| II 8% glycerol alone as drinking water | 0 | 0 | 0 |
| III 4NQO + water alone as drinking water | 3 | 0.2 | 13.3 |
| IV 4NQO + 8% glycerol alone as drinking water | 48 | 3.2 | 100 |
| V 4NQO + 8% glycerol containing 0.1 ng/ml of NFD as drinking water | 9 | 0.6 | 33.3 |

EXAMPLE 4

Inhibition of Two-step Skin Carcinogenesis in Mice Skin

Female ICR mice were used as test animals. Fifteen mice were housed in a cage and kept on a commercial pellet diet and drinking water ad libitum until the end of the experiment. The mice were purchased at their age of six-week-old. Dorsal hair of mice was shaved, and next day, 390 nmol of 7,12-dimethylbenz(a)anthracene (DMBA) in 0.1 ml acetone was applied, as an initiator, on the shaved back. One week later, 1.7 nmol of 12-O-tetradecanoylphorbol-13-acetate (TPA) in 0.1 ml acetone was applied, as a promoter, to the same place twice a week. This procedure was repeated for 20 weeks. One hour before the TPA treatment, each group consisting of 15 mice was subjected to dermal application of 0.1 mi of acetone or 85 nmol NFD in 0.1 ml acetone, and the inhibitory effect of NFD on the skin carcinogenesis was measured.

Mice were observed once a week for the number of papillomas larger than 1 mm, and the experimental results were given as the percentage of papilloma-bearing mice in each group and the number of papillomas per mouse.

Figure 28B:
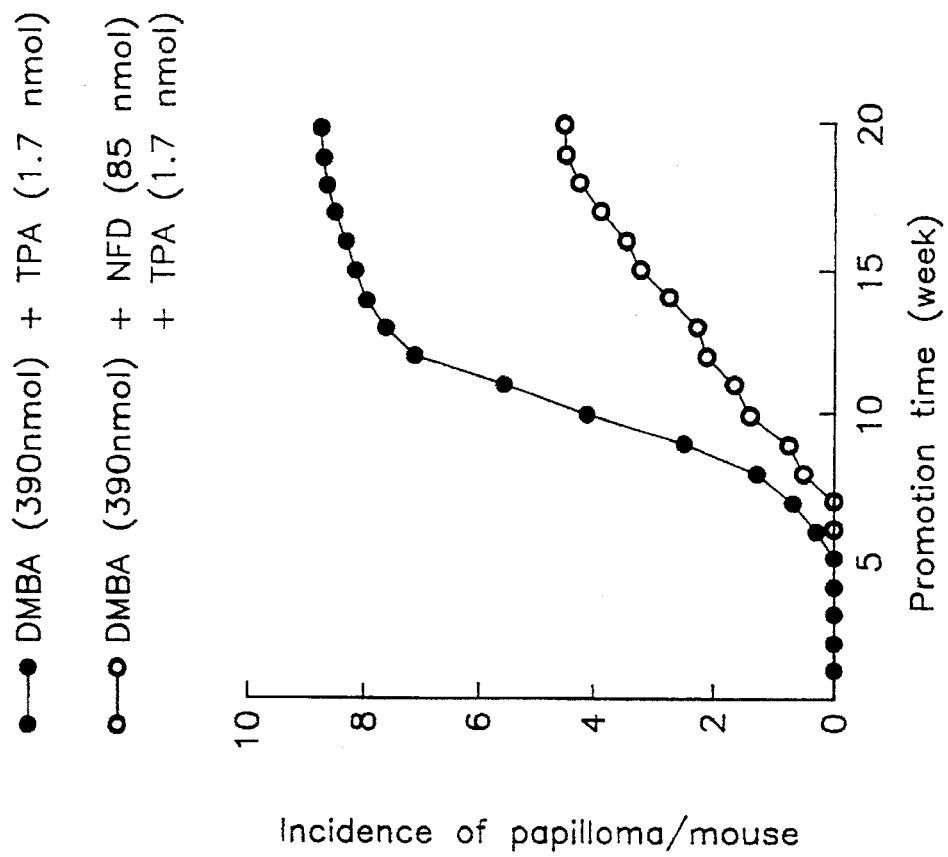
FIG. 28 shows the inhibitory effect of NFD on carcinogenic promotion.
Figure 28A:
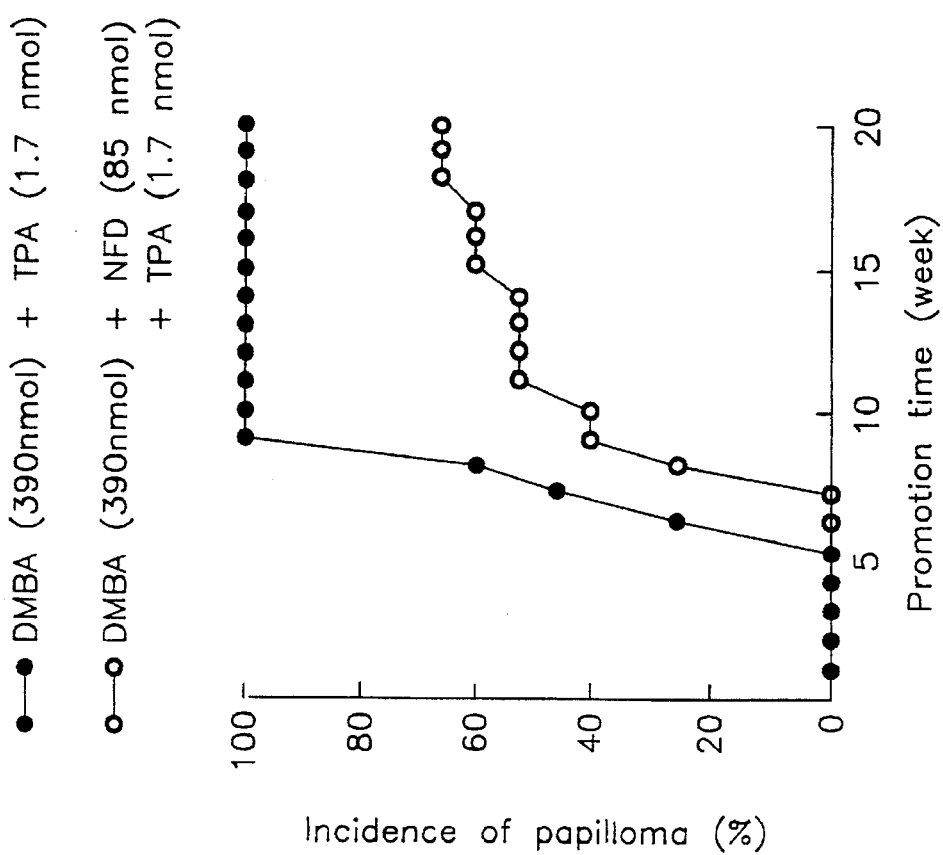
Figure 29A:
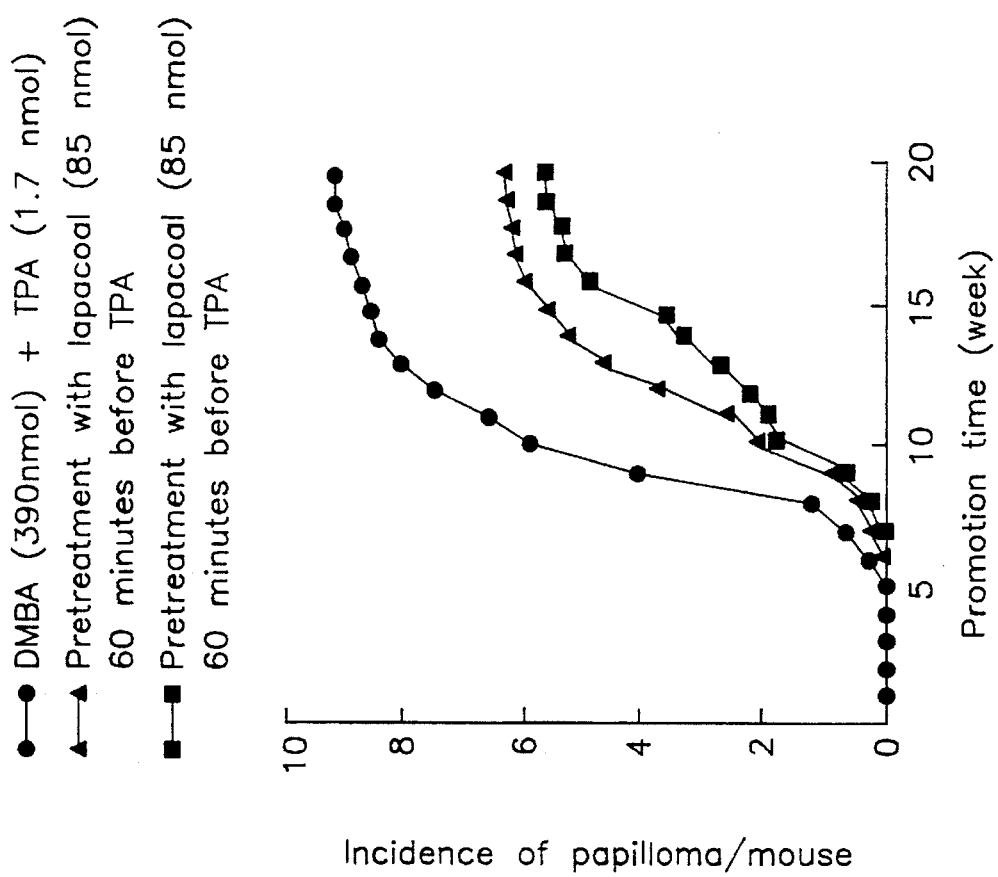
FIG. 29 shows the inhibitory effect of lapacoal, an active control, on carcinogenic promotion.
Figure 29B:
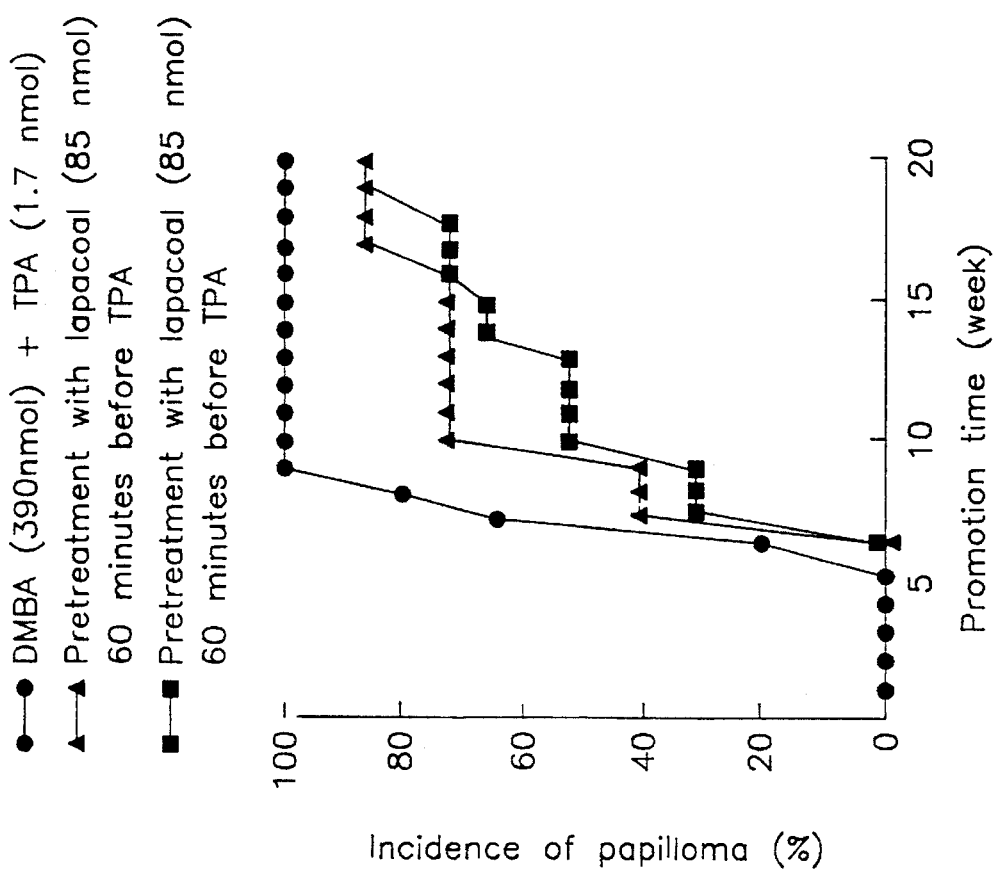

FIG. 28 shows the inhibitory effect of NFD, and FIG. 29 shows the inhibitory effect of lapacoal used as a positive control.

Examples 3 and 4 demonstrate that NFD can be used as an inhibitor of carcinogenic promotion and may be useful as an antitumor agent.

When NFD is used as an antitumor agent, it is desirous to orally administer NFD three times a day. Preferable daily dose of NFD is 0.15–1.5 mg for adults and ½ and ⅙ amount of the adult dose for children and young infants, respectively. NFD can be administered both orally and parenterally, but the oral administration is preferable.

Pharmaceutical Formulation

To 1.5 mg of NFD, 66.5 mg of lactose as a vehicle, 10 mg of starch paste as a binder, 20 mg of starch as a disintegrant, and 2 mg of magnesium stearate as a tablet lubricant were added, mixed thoroughly and compressed to give 100 mg tablets containing 1.5 mg of NFD (total: 100 mg).

We claim:

1. A method for treating a malignant tumor sensitive to treatment with a compound in a mammal, which comprises administering to said mammal an effective amount of the compound, which is 2-(1-hydroxyethyl)-5-hydroxynaphtho[2,3-b]furan-4,9-dione of the following formula:

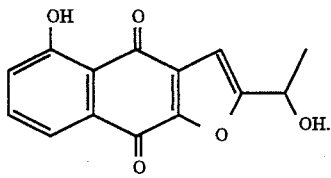

2. A method of claim 1 wherein the malignant tumor is an adenocarcinoma selected from the group consisting of a human lung adenocarcinoma and a human colon adenocarcinoma.

3. A method of claim 1 wherein the malignant tumor is a carcinoma selected from the group consisting of squamous cell carcinoma, cervical carcinoma, pancreatic carcinoma, lung carcinoma, bladder carcinoma, renal cell carcinoma, thyroid carcinoma, cholangiocarcinoma, ovarian carcinoma and chorio carcinoma.

4. A method of claim 1 wherein the malignant tumor prostate cancer.

5. A method of claim 1 wherein the malignant tumor is melanoma.

6. A method of claim 1 wherein the malignant tumor is lymphoma.

7. A method of claim 1 wherein the malignant tumor is leukemia.

8. A method of claim 1 wherein the malignant tumor is neuroblastoma.

9. A method of claim 1 wherein the malignant tumor is gastric cancer.

10. A method of claim 1 wherein the malignant tumor is breast cancer.

11. A method of claim 1 wherein the malignant tumor is hepatoma.

12. A method of claim 1 wherein the malignant tumor is human lung squamous epithelioma.

* * * * *